(12) United States Patent
Ishii et al.

(10) Patent No.: US 7,368,615 B2
(45) Date of Patent: May 6, 2008

(54) CATALYST COMPRISING A CYCLIC IMIDE COMPOUND AND PROCESS FOR PRODUCING ORGANIC COMPOUNDS USING THE CATALYST

(75) Inventors: Yasutaka Ishii, Takatsuki (JP); Tatsuya Nakano, Himeji (JP); Shinya Nagano, Himeji (JP); Naoto Okuyama, Himeji (JP)

(73) Assignee: Daicel Chemical Industries, Ltd., Sakai-shi (JP)

( * ) Notice: Subject to any disclaimer, the term of this patent is extended or adjusted under 35 U.S.C. 154(b) by 35 days.

(21) Appl. No.: 11/242,779

(22) Filed: Oct. 5, 2005

(65) Prior Publication Data

US 2006/0036100 A1 Feb. 16, 2006

Related U.S. Application Data

(62) Division of application No. 10/092,554, filed on Mar. 8, 2002, now Pat. No. 6,998,491.

(30) Foreign Application Priority Data

Mar. 9, 2001 (JP) .............................. 2001-067633

(51) Int. Cl.
*C07C 13/00* (2006.01)
(52) U.S. Cl. ................. 585/20; 548/402; 501/167
(58) Field of Classification Search .......... 585/20; 548/402; 502/167
See application file for complete search history.

(56) References Cited

U.S. PATENT DOCUMENTS 6,232,258 B1 5/2001 Ishii et al.

FOREIGN PATENT DOCUMENTS

| EP | 0 824 962 A1 | 2/1998 |
|---|---|---|
| EP | 0 864 555 A1 | 9/1998 |
| EP | 0 878 458 A1 | 11/1998 |
| EP | 0 879 812 A1 | 11/1998 |
| EP | 0 897 747 A1 | 2/1999 |
| EP | 1 004 566 A2 | 5/2000 |
| EP | 1 004 566 A3 | 5/2000 |
| EP | 1 036 788 A1 | 9/2000 |
| EP | 1 074 537 A1 | 2/2001 |
| EP | 1 342 715 A2 | 9/2003 |
| EP | 1 055 654 A1 | 11/2004 |
| JP | 8-38909 A | 2/1996 |
| WO | WO 00/69803 | * 11/2000 |

OTHER PUBLICATIONS

Ishii et al., 2000, CAS: 134:4527.*
Sawatari et al., *J. Org. Chem.*, vol. 66, (2001), pp. 7889-7891.
Ishii et al., *J. Org. Chem.*, vol. 61, (1996), pp. 4520-4526.
Fedors, *Polymer Engineering and Science*, vol. 14, No. 2, (Feb. 1974), pp. 147-154.
Sakaguchi et al., *Technology Reports of Kansai University*, Osaka, Japan, No. 38, (Mar. 1996), pp. 123-131, XP002067301.
Gorgy et al., *Electrochimica Acta*, vol. 44, (1998), pp. 385-393.

* cited by examiner

*Primary Examiner*—Rei-tsang Shiao
(74) *Attorney, Agent, or Firm*—Birch, Stewart, Kolasch & Birch, LLP

(57) ABSTRACT

A catalyst includes a cyclic imide compound having an N-substituted cyclic imide skeleton represented by following Formula (I):

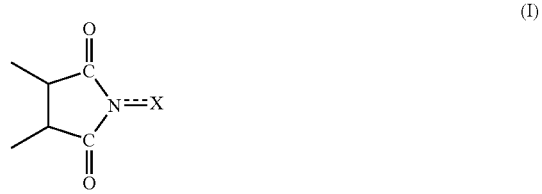

wherein X is an oxygen atom or a hydroxyl group, and having a solubility parameter of less than or equal to 26 $[(MPa)^{1/2}]$ as determined by Fedors method. The catalyst may further comprise a metallic compound. By allowing (A) a compound capable of forming a radical to react with (B) a radical scavenging compound in the presence of the catalyst, an addition or substitution reaction product between the compound (A) and the compound (B) or a derivative thereof can be obtained.

4 Claims, No Drawings

US 7,368,615 B2

CATALYST COMPRISING A CYCLIC IMIDE COMPOUND AND PROCESS FOR PRODUCING ORGANIC COMPOUNDS USING THE CATALYST

This application is a Divisional of application Ser. No. 10/092,554 filed on Mar. 8, 2002, now U.S. Pat. No. 6,998,491 B2, and for which priority is claimed under 35 U.S.C. § 120; and this application claims priority of Application No. 2001-067633 filed in Japan on Mar. 9, 2001 under 35 U.S.C. § 119; the entire contents of all are hereby incorporated by reference.

BACKGROUND OF THE INVENTION

1. Field of the Invention

The present invention relates to a catalyst that is useful for oxidation, nitration, carboxylation, reactions for the formation of a carbon-carbon bond and other reactions, and to a process for producing an organic compound using the catalyst.

2. Description of the Related Art

An oxidation reaction is one of the most essential reactions in the field of organic chemical industry, and various oxidation processes have been developed. To save resources and to reduce environmental issues, catalytic oxidation processes using molecular oxygen or air directly as an oxidizing agent are preferred. However, such catalytic oxidation processes generally require high temperatures and/or high pressures for the activation of oxygen or, alternatively, must be performed in the co-existence of a reducing agent such as an aldehyde to proceed the reaction under mild conditions. Accordingly, these conventional catalytic oxidation processes cannot easily and efficiently produce alcohols or carboxylic acids under mild conditions.

Lower hydrocarbons such as methane and ethane are nitrated using nitric acid or nitrogen dioxide at high temperatures of from 250° C. to 300° C. However, when a hydrocarbon having a large number of carbon atoms is nitrated under the above condition, the substrate is decomposed, and a target nitro compound cannot be obtained in a high yield. To nitrate hydrocarbons, a method using mixed acid (a mixture of nitric acid and sulfuric acid) is widely employed. However, this method requires large amounts of strong acids in high concentrations.

Additionally, few processes are known for efficiently and directly introducing carboxyl groups into hydrocarbons under mild conditions.

Organic sulfur acids or salts thereof can be produced by various processes. For example, processes for producing a sulfonic acid include a process of oxidizing a thiol or disulfide with an oxidizing agent, a process of allowing an aromatic hydrocarbon to react with anhydrous $SO_3$-pyridine or chlorosulfuric acid by using a Friedel-Crafts reaction, and a process of synthetically obtaining a sulfonic acid by subjecting an unsaturated compound to free-radical addition. These processes, however, require extreme reaction conditions or inevitably produce large amounts of by-products. Additionally, no processes for directly and efficiently sulfonating non-aromatic hydrocarbons have been known.

Some processes yield useful organic compounds by adding compounds to unsaturated compounds each having a carbon-carbon double bond or heteroatom-containing compounds. For example, by allowing an active methylene compound such as a malonic diester to react with an olefin having an electron attractive group, such as acrylonitrile, in the presence of a base, a carbon-carbon bond is formed as a result of a nucleophilic addition reaction and thereby yields an addition product (Michael addition reaction). By treating two types of carbonyl compounds in the presence of an acid or a base, one carbonyl compound is nucleophilically added to the other to form a carbon-carbon bond and thereby yields an aldol condensate.

These processes, however, are generally performed in the presence of an acid or base and cannot be applied to compounds each having a substituent that is susceptible to the acid or base. In addition, these processes cannot allow, for example, a hydroxymethyl group, an alkoxymethyl group, an acyl group or a tertiary carbon atom to directly combine with a carbon atom constituting an unsaturated bond of an unsaturated compound or with a methine carbon atom of a bridged cyclic compound.

Addition reactions to carbon-carbon double bonds in accordance with radical mechanisms or coupling reactions to form carbon-carbon bonds are also known. However, there are few processes that can efficiently yield addition or substitution reaction products or derivatives thereof by action of, for example, molecular oxygen under mild conditions.

Hydroxy-γ-butyrolactone derivatives can be produced by some processes. For example, European Patent Publication No. EP-A-2103686 discloses a process in which glyoxylic acid is allowed to react with isobutylene and thereby yields pantolactone. Likewise, Japanese Unexamined Patent Application Publication No. 61-282373 discloses a process in which hydrated glyoxylic acid is allowed to react with t-butyl alcohol and thereby yields pantolactone. Tetrahedron, 933 (1979) discloses a process for synthetically obtaining pantolactone. This process includes the steps of hydrolyzing 4-hydroxy-2-methyl-5,5,5-trichloro-1-pentene to yield 2-hydroxy-4-methyl-4-pentenoic acid and cyclizing this compound in the presence of hydrochloric acid. In addition, The Chemical Society of Japan, Spring Conference Proceedings II, pp. 1015 (1998) reports that light irradiation to a mixture containing an α-acetoxy-α,β-unsaturated carboxylic ester and 2-propanol yields a corresponding α-acetoxy-γ,γ-dimethyl-γ-butyrolactone derivative. However, these processes employ raw materials that are not easily available or require special conditions for the reactions.

Japanese Unexamined Patent Application Publications No. 8-38909 and No. 9-327626 propose oxidation catalysts each comprising an imide compound having a specific structure or the imide compound in combination with, for example, a transition metal compound. The catalysts are used for oxidizing an organic substrate with molecular oxygen. Japanese Unexamined Patent Application Publication No. 11-239730 discloses a process, in which a substrate is allowed to react with at least one reacting agent selected from (i) nitrogen oxides and (ii) mixtures of carbon monoxide and oxygen in the presence of the cyclic imide compound and thereby introduces at least one functional group selected from nitro group and carboxyl group into the substrate. PCT International Publication Number WO 00/35835 discloses a process, in which two compounds are allowed to react with each other in the presence of a specific imide compound and a radical generator with respect to the imide compound and thereby yield an addition or substitution reaction product or an oxidized product thereof in accordance with a radical mechanism. The processes using these imide compounds can introduce oxygen-atom-containing groups such as hydroxyl group, nitro group and carboxyl group into substrates or can form carbon-carbon bonds under relatively mild conditions. However, they are still insufficient in reaction rates or yields of the target compounds in reactions in the absence of solvents or in the presence of nonpolar solvents due to their low solubility in the reaction systems in question.

SUMMARY OF THE INVENTION

Accordingly, an object of the present invention is to provide a catalyst that can yield an organic compound in a high yield as a result of, for example, an addition or substitution reaction under mild conditions even in reactions in the absence of solvents or in the presence of nonpolar solvents and to provide a process for producing an organic compound using the catalyst.

Another object of the present invention is to provide a catalyst that can smoothly introduce an oxygen-atom-containing group into a substrate even in reactions in the absence of solvents or in the presence of nonpolar solvents and to provide a process for producing an organic compound using the catalyst.

Yet another object of the present invention is to provide a catalyst that is highly stable and can maintain its catalytic activity over a long time.

A further object of the present invention is to provide a radical reaction catalyst that exhibits high catalytic activity even in a small amount.

After intensive investigations to achieve the above objects, the present inventors have found that, when a compound capable of forming a radical is allowed to react with a radical scavenging compound in the presence of a specific cyclic imide compound, a corresponding addition or substitution reaction product or a derivative thereof can be obtained in a high yield even in reactions in the absence of solvents or in the presence of nonpolar solvents. The present invention has been accomplished based on these findings.

Specifically, the present invention provides, in an aspect, a catalyst including a cyclic imide compound. The cyclic imide compound has a N-substituted cyclic imide skeleton represented by following Formula (I):

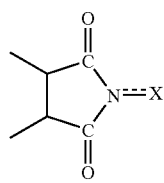

(I)

wherein X is an oxygen atom or a hydroxyl group, and has a solubility parameter of less than or equal to 26 (MPa)$^{1/2}$ as determined by Fedors method.

The cyclic imide compound includes, for example, a compound represented by following Formula (1):

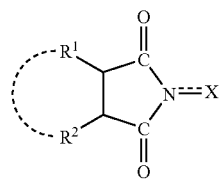

(1)

wherein R$^1$ and R$^2$ are the same or different and are each a hydrogen atom, a halogen atom, an alkyl group, an aryl group, a cycloalkyl group, a hydroxyl group, an alkoxy group, a carboxyl group, a substituted oxycarbonyl group, an acyl group or an acyloxy group, where R$^1$ and R$^2$ may be combined to form a double bond or an aromatic or non-aromatic ring; one or two of N-substituted cyclic imido group indicated in Formula (1) may be further formed on R$^1$, R$^2$, or on the double bond or aromatic or non-aromatic ring formed by R$^1$ and R$^2$; and X is an oxygen atom or a hydroxyl group.

In another aspect, the present invention provides a catalyst including a cyclic imide compound represented by following Formula (II):

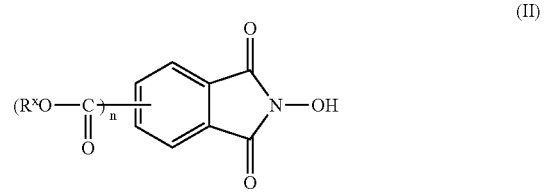

(II)

wherein R$^x$ is a hydrocarbon group having five or more carbon atoms; and n denotes an integer of from 1 to 4, where the groups —C(=O)—OR$^x$ may be the same or different when n is equal to or more than 2.

The above catalysts may further include a metallic compound in combination with the cyclic imide compound.

In a further aspect, the present invention provides a process for producing an organic compound. The process includes the step of allowing (A) a compound capable of forming a radical to react with (B) a radical scavenging compound in the presence of any of the above catalysts to thereby yield an addition or substitution reaction product between the compound (A) and the compound (B) or a derivative thereof.

Such compounds (A) capable of forming a radical include, for example, (A1) heteroatom-containing compounds each having a carbon-hydrogen bond at the adjacent position to the heteroatom, (A2) compounds each having a carbon-heteroatom double bond, (A3) compounds each having a methine carbon atom, (A4) compounds each having a carbon-hydrogen bond at the adjacent position to an unsaturated bond, (A5) non-aromatic cyclic hydrocarbons, (A6) conjugated compounds, (A7) amines, (A8) aromatic compounds, (A9) straight-chain alkanes and (A10) olefins.

Such radical scavenging compounds (B) may be selected from (B1) unsaturated compounds, (B2) compounds each having a methine carbon atom, (B3) heteroatom-containing compounds, and (B4) oxygen-atom-containing reacting agents. The oxygen-atom-containing reacting agents (B4) include, for example, oxygen, carbon monoxide, nitrogen oxide and sulfur oxides, as well as nitric acid, nitrous acid and salts thereof.

The reactions between the compound (A) capable of forming a radical and the radical scavenging compound (B) include, for example, oxidation reactions, carboxylation reactions, nitration reactions, sulfonation reactions, coupling reactions and combinations thereof.

The term "addition or substitution" reaction as used herein is used in a broad meaning and also includes, for example, oxidation and sulfonation.

The process of the present invention can produce, for example, organic compounds each having an oxygen-atom-containing group, carbon-carbon bond-formed products or derivatives thereof (e.g., cyclized derivatives) in high yields as a result of addition or substitution reactions under mild conditions, even when reactions are performed in the absence of solvents or in the presence of non-polar solvents. Such oxygen-atom-containing groups include, for example, hydroxyl group, oxo group, carboxyl group, nitro group and sulfonic acid group. In addition, the process can smoothly introduce such oxygen-atom-containing groups into organic substrates even in the absence of solvents or in the presence of non-polar solvents.

The catalysts of the present invention are highly stable and can maintain their catalytic activity over a long time. In addition, the catalysts exhibit high catalytic activity in radical reactions even in small amounts.

DESCRIPTION OF THE PREFERRED EMBODIMENTS

Cyclic Imide Compounds

A catalyst of the present invention comprises a cyclic imide compound having an N-substituted cyclic imide skeleton represented by Formula (I) and having a solubility parameter of less than or equal to 26 $(MPa)^{1/2}$ (for example, from about 15 to about 26 $(MPa)^{1/2}$) as determined by Fedors method. The cyclic imide compound may have a plurality of the N-substituted cyclic imide skeleton represented by Formula (I) in the molecule.

Examples of the cyclic imide compound include imide compounds represented by Formula (1). Of the substituents $R^1$ and $R^2$ in these cyclic imide compounds, the halogen atom includes iodine, bromine, chlorine and fluorine atoms. The alkyl group includes, but is not limited to, methyl, ethyl, propyl, isopropyl, butyl, isobutyl, s-butyl, t-butyl, hexyl, decyl, dodecyl, tetradecyl, hexadecyl, and other straight- or branched-chain alkyl groups each having from about 1 to about 30 carbon atoms, of which alkyl groups each having from about 1 to about 20 carbon atoms are preferred.

The aryl group includes, for example, phenyl and naphthyl groups, and the cycloalkyl group includes, for example, cyclopentyl and cyclohexyl groups. The alkoxy group includes, but is not limited to, methoxy, ethoxy, isopropoxy, butoxy, t-butoxy, hexyloxy, octyloxy, decyloxy, dodecyloxy, tetradecyloxy, octadecyloxy, and other alkoxy groups each having from about 1 to about 30 carbon atoms, of which alkoxy groups each having from about 1 to about 20 carbon atoms are preferred.

The substituted oxycarbonyl group includes, but is not limited to, methoxycarbonyl, ethoxycarbonyl, isopropoxycarbonyl, butoxycarbonyl, t-butoxycarbonyl, hexyloxycarbonyl, heptyloxycarbonyl, octyloxycarbonyl, decyloxycarbonyl, dodecyloxycarbonyl, tetradecyloxycarbonyl, hexadecyloxycarbonyl, octadecyloxycarbonyl, and other alkoxycarbonyl groups (preferably, $C_1$-$C_{30}$ alkoxy-carbonyl groups); cyclopentyloxycarbonyl, cyclohexyloxycarbonyl, and other cycloalkyloxycarbonyl groups (preferably, 3- to 20-membered cycloalkyloxycarbonyl groups); phenyloxycarbonyl, naphthyloxycarbonyl, and other aryloxycarbonyl groups (preferably, $C_6$-$C_{20}$ aryloxy-carbonyl groups); and benzyloxycarbonyl and other aralkyloxycarbonyl groups (preferably, $C_7$-$C_{21}$ aralkyloxy-carbonyl groups).

The acyl group includes, but is not limited to, formyl, acetyl, propionyl, butyryl, isobutyryl, valeryl, pivaloyl, hexanoyl, heptanoyl, octanoyl, nonanoyl, decanoyl, lauroyl, myristoyl, palmitoyl, stearoyl, and other $C_1$-$C_{30}$ aliphatic acyl groups (preferably, $C_1$-$C_{20}$ aliphatic acyl groups), and other saturated or unsaturated aliphatic acyl groups; acetoacetyl group; cyclopentanecarbonyl, cyclohexanecarbonyl, and other cycloalkanecarbonyl groups and other alicyclic acyl groups; benzoyl, naphthoyl, and other aromatic acyl groups.

The acyloxy group includes, but is not limited to, formyloxy, acetyloxy, propionyloxy, butyryloxy, isobutyryloxy, valeryloxy, pivaloyloxy, hexanoyloxy, heptanoyloxy, octanoyloxy, nonanoyloxy, decanoyloxy, lauroyloxy, myristoyloxy, palmitoyloxy, stearoyloxy, and other $C_1$-$C_{30}$ aliphatic acyloxy groups (preferably, $C_1$-$C_{20}$ aliphatic acyloxy groups), and other saturated or unsaturated aliphatic acyloxy groups; acetoacetyloxy group; cyclopentanecarbonyloxy, cyclohexanecarbonyloxy, and other cycloalkanecarbonyloxy groups and other alicyclic acyloxy groups; benzoyloxy, naphthoyloxy, and other aromatic acyloxy groups.

The substituents $R^1$ and $R^2$ may be identical to or different from each other. The substituents $R^1$ and $R^2$ may be combined to form a double bond, or an aromatic or non-aromatic ring. The preferred aromatic or non-aromatic ring is a 5- to 12-membered ring, and especially a 6- to 10-membered ring. The ring may be a heterocyclic ring or condensed heterocyclic ring, but it is often a hydrocarbon ring. Such rings include, but are not limited to, non-aromatic alicyclic rings (e.g., cyclohexane ring and other cycloalkane rings which may have a substituent, cyclohexene ring and other cycloalkene rings which may have a substituent), non-aromatic bridged rings (e.g., 5-norbornene ring and other bridged hydrocarbon rings which may have a substituent), benzene ring, naphthalene ring, and other aromatic rings (including condensed rings) which may have a substituent. The ring is composed of an aromatic ring in many cases. The ring may have at least one substituent. Such substituents include, for example, alkyl groups, haloalkyl groups, hydroxyl group, alkoxy groups, carboxyl group, alkoxycarbonyl groups, acyl groups, acyloxy groups, nitro group, cyano group, amino groups, and halogen atoms.

One or two of the N-substituted cyclic imido group indicated in Formula (1) may be further formed on $R^1$, $R^2$ or on the double bond or aromatic or non-aromatic ring formed by $R^1$ and $R^2$. For example, when $R^1$ or $R^2$ is an alkyl group having two or more carbon atoms, the N-substituted cyclic imido group may be formed with the adjacent two carbon atoms constituting the alkyl group. Likewise, when $R^1$ and $R^2$ are combined to form a double bond, the N-substituted cyclic imido group may be formed with the double bond. When $R^1$ and $R^2$ are combined to form an aromatic or non-aromatic ring, the N-substituted cyclic imido group may be formed with the adjacent two carbon atoms constituting the ring.

Preferred cyclic imide compounds include compounds of the following formulae:

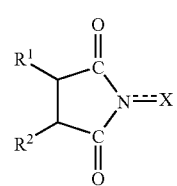

(1a)

-continued

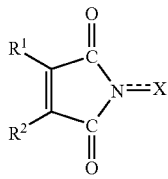
(1b)

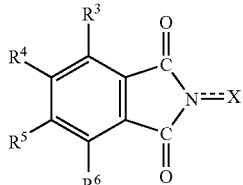
(1c)

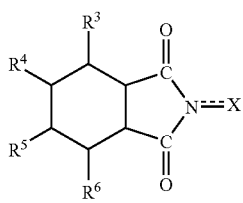
(1d)

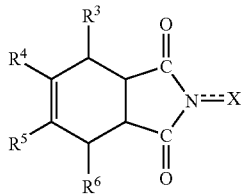
(1e)

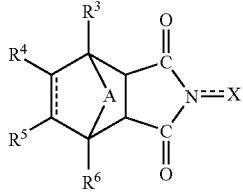
(1f)

wherein $R^3$, $R^4$, $R^5$ and $R^6$ are the same or different and are each a hydrogen atom, an alkyl group, a haloalkyl group, a hydroxyl group, an alkoxy group, a carboxyl group, a substituted oxycarbonyl group, an acyl group, an acyloxy group, a nitro group, a cyano group, an amino group or a halogen atom, where adjacent groups of $R^3$ to $R^6$ may be combined to form an aromatic or non-aromatic ring; A in Formula (1f) is a methylene group or an oxygen atom; and $R^1$, $R^2$ and X have the same meanings as defined above, where one or two of the N-substituted cyclic imido group indicated in Formula (1c) may be further formed on the benzene ring in Formula (1c).

In the substituents $R^3$ to $R^6$, the alkyl group includes similar alkyl groups to those exemplified above. The haloalkyl group includes, for example, trifluoromethyl group and other haloalkyl groups each having from about 1 to about 30 carbon atoms and preferably from about 1 to about 20 carbon atoms. The alkoxy group includes similar alkoxy groups to those mentioned above, and the substituted oxycarbonyl group includes similar substituted oxycarbonyl groups (e.g., alkoxycarbonyl groups, cycloalkyloxycarbonyl groups, aryloxycarbonyl groups and aralkyloxycarbonyl groups) to those exemplified above. The acyl group includes similar acyl groups (e.g., saturated or unsaturated aliphatic acyl groups, acetoacetyl group, alicyclic acyl groups and aromatic acyl groups) to those mentioned above. The acyloxy group includes similar acyloxy groups (e.g., saturated or unsaturated aliphatic acyloxy groups, acetoacetyloxy group, alicyclic acyloxy groups and aromatic acyloxy groups) to those mentioned above. The halogen atom includes fluorine, chlorine and bromine atoms. Each of the substituents $R^3$ to $R^6$ is generally a hydrogen atom, an alkyl group, a carboxyl group, a substituted oxycarbonyl group, a nitro group or a halogen atom. The ring formed by the adjacent groups of $R^3$ to $R^6$ includes similar rings to the rings formed by $R^1$ and $R^2$. Among them, aromatic or non-aromatic 5- to 12-membered rings are preferred.

The solubility parameter as determined by Fedors method [SP; the parameter of an oxygen atom (—O—) constituting an ester bond, energy of vaporization: 3350 J/mol, molar volume: 3.8 cm$^3$/mol] can be determined by methods described in literature [R. F. Fedors, Polym. Eng. Sci., 14(2), 147(1974); E. A. Grulke, Polymer Handbook, VII/675; Yuji HARAZAKI, Painting Technology, 3, 129(1987)]. The catalyst of the present invention has a SP of less than or equal to 26 (MPa)$^{1/2}$ and is highly soluble even in reactions in the absence of solvents or in the presence of low-polar solvents. Accordingly, the catalyst effectively acts upon the substrate and proceeds the reaction smoothly to thereby effectively yield a target compound. The catalyst preferably has SP of less than or equal to 25.5 (e.g., from about 15 to about 25.5) (MPa)$^{1/2}$.

The present invention also includes a catalyst comprising the cyclic imide compound represented by Formula (II). In $R^x$ in Formula (II), the hydrocarbon group having five or more carbon atoms includes, but is not limited to, pentyl, isopentyl, hexyl, isohexyl, heptyl, octyl, 2-ethylhexyl, nonyl, decyl, dodecyl, tetradecyl, hexadecyl, and other alkyl groups (e.g., $C_5$-$C_{20}$ alkyl groups); cyclopentyl, cyclohexyl, methylcyclohexyl, cyclooctyl, cyclodecyl, cyclododecyl, and other cycloalkyl groups (e.g., 5- to 20-membered cycloalkyl groups); phenyl, tolyl, naphthyl, and other aryl groups (e.g., $C_6$-$C_{20}$ aryl groups); benzyl, 2-phenylethyl, and other aralkyl groups (e.g., $C_7$-$C_2$, aralkyl groups). Among them, $C_6$-$C_{20}$ alkyl groups (specifically $C_8$-$C_{16}$ alkyl groups), 5- or 6-membered cycloalkyl groups and $C_6$-$C_{10}$ aryl groups are preferred as $R^x$.

In Formula (II), n denotes an integer from 1 to 4, where the groups —C(=O)—OR$^x$ may be the same or different when n is equal to or more than 2. The number n is preferably 1 or 2.

Preferred examples of cyclic imide compounds for use in the catalysts of the present invention are α,β-bis(pentanoyloxy)-N-hydroxysuccinimide (SP: 25.3), α,β-bis(hexanoyloxy)-N-hydroxysuccinimide (SP: 24.5), α,β-bis(octanoyloxy)-N-hydroxysuccinimide (SP: 23.4), α,β-bis(decanoyloxy)-N-hydroxysuccinimide (SP: 22.6), α,β-bis(lauroyloxy)-N-hydroxysuccinimide (SP: 22.0), α,β-bis(myristoyloxy)-N-hydroxysuccinimide, α,β-bis(palmitoyloxy)-N-hydroxysuccinimide, α,β-bis(stearoyloxy)-N-hydroxysuccinimide, α,β-bis(cyclopentanecarbonyloxy)-N-hydroxysuccinimide, α,β-bis(cyclohexanecarbonyloxy)-N-hydroxysuccinimide, α,β-bis(benzoyloxy)-N-hydroxysuccinimide, and other compounds of Formula (1) wherein $R^1$ and $R^2$ are acyloxy groups (preferably $C_5$-$C_{30}$ aliphatic acyloxy groups, alicyclic acyloxy groups or aromatic acyloxy groups; and more preferably $C_6$-$C_{20}$ aliphatic acyloxy groups, cyclohexanecarbonyl groups or benzoyloxy groups); N-hydroxy-4-pentyloxycarbonylphthalimide (SP: 28.2), N-hydroxy-4-hexyloxycarbonylphthalimide (SP: 27.5), N-hydroxy-4-octyloxycarbonylphthalimide (SP: 26.4), N-hydroxy-4-decyloxycarbonylphthalimide (SP: 25.4) N-hydroxy-4-dodecyloxycarbonylphthalimide (SP: 24.7) N-hydroxy-4-tetradecyloxycarbonylphthalimide, N-hydroxy-4-hexadecyloxycarbonylphthalimide, N-hydroxy-4-octadecyloxycarbonylphthalimide, N-hydroxy-4-cyclopentyloxycarbonylphthalimide, N-hydroxy-4-cyclohexyloxycarbonylphthalimide, N-hydroxy-4-phenoxycarbonylphthalimide, N-hydroxy-4-benzyloxycarbonylphthalimide, and other compounds of Formula (1c), where $R^3=R^5=R^6=H$; and $R^4$ is a substituted oxycarbonyl group (preferably a $C_5$-$C_{30}$ alkoxy-carbonyl group, a cycloalkyloxycarbonyl group or an aryloxycarbonyl group; and more preferably a $C_6$-$C_{20}$ alkoxy-carbonyl group, a cyclohexyloxycarbonyl group or a phenoxycarbonyl group); N-hydroxy-4,5-bis(pentyloxycarbonyl)phthalimide (SP: 26.3), N-hydroxy-4,5-bis(hexyloxycarbonyl)phthalimide (SP: 25.5), N-hydroxy-4,5-bis(octyloxycarbonyl)phthalimide (SP: 24.5), N-hydroxy-4,5-bis(decyloxycarbonyl)phthalimide (SP: 23.5), N-hydroxy-4,5-bis(dodecyloxycarbonyl)phthalimide (SP: 22.8), N-hydroxy-4,5-bis (tetradecyloxycarbonyl)phthalimide, N-hydroxy-4,5-bis(hexadecyloxycarbonyl)phthalimide, N-hydroxy-4,5-bis(octadecyloxycarbonyl)phthalimide, N-hydroxy-4,5-bis(cyclopentyloxycarbonyl)phthalimide, N-hydroxy-4,5-bis(cyclohexyloxycarbonyl)phthalimide, N-hydroxy-4,5-bis(phenoxycarbonyl)phthalimide, N-hydroxy-4,5-bis(benzyloxycarbonyl)phthalimide, and other compounds of Formula (1c) where $R^3=R^6=H$; and $R^4$ and $R^5$ are each a substituted oxycarbonyl groups (preferably, a $C_5$-$C_{30}$ alkoxy-carbonyl group, a cycloalkyloxycarbonyl group or an aryloxycarbonyl group; and more preferably a $C_6$-$C_{20}$ alkoxy-carbonyl group, a cyclohexyloxycarbonyl group or a phenoxycarbonyl group). The SPs in parentheses are expressed in the unit of $(MPa)^{1/2}$.

The cyclic imide compounds can be obtained by a conventional imidization process (a process for the formation of an imide), such as a process that comprises the steps of allowing a corresponding acid anhydride to react with hydroxylamine for ring-opening of an acid anhydride group, and closing the ring to form an imide. Each of the cyclic imide compounds can be used alone or in combination in the reaction. The cyclic imide compounds may be formed in the reaction system.

The amount of the cyclic imide compound can be selected within a wide range and is, for example, from about 0.0000001 to about 1 mole, preferably from about 0.00001 to about 0.5 mole, more preferably from about 0.0001 to about 0.4 mole, and often from about 0.001 to about 0.35 mole, relative to 1 mole of the reactant (substrate).

Promoters (Co-catalysts)

According to the invention, a promoter (co-catalyst) can be used in combination with the cyclic imide compound. Such promoters include, for example, metallic compounds. By using the catalytic cyclic imide compound in combination with the metallic compound, the rate and/or selectivity of the reaction can be improved.

Metallic elements constituting the metallic compounds are not specifically limited and are often metallic elements of the Groups 2 to 15 of the Periodic Table of Elements. The term "metallic element" as used herein also includes boron B. Examples of the metallic elements include, of the Periodic Table of Elements, Group 2 elements (e.g., Mg, Ca, Sr and Ba), Groups 3 elements (e.g., Sc, lanthanoid elements and actinoid elements), Group 4 elements (e.g., Ti, Zr and Hf), Group 5 elements (e.g., V), Group 6 elements (e.g., Cr, Mo and W), Group 7 elements (e.g., Mn), Group 8 elements (e.g., Fe and Ru), Group 9 elements (e.g., Co and Rh), Group 10 elements (e.g., Ni, Pd and Pt), Group 11 elements (e.g., Cu), Group 12 elements (e.g., Zn), Groups 13 elements (e.g., B, Al and In), Group 14 elements (e.g., Sn and Pb) and Group 15 elements (e.g., Sb and Bi). Preferred metallic elements include transition metal elements (elements of Groups 3 to 12 of the Periodic Table of Elements). Among them, elements of the Groups 5 to 11 of the Periodic Table of Elements are specifically preferred, of which elements of Groups 5 to 9 are typically preferred. Especially, V, Mo, Mn and Co are preferred. The valency of the metallic element is not specifically limited and is, for example, from about 0 to about 6.

Such metallic compounds include, but are not limited to, elementary substances, hydroxides, oxides (including complex oxides), halides (fluorides, chlorides, bromides and iodides), salts of oxoacids (e.g., nitrates, sulfates, phosphates, borates, and carbonates), salts of isopolyacids, salts of heteropolyacids, and other inorganic compounds of the aforementioned metallic elements; salts of organic acids (e.g., acetates, propionates, prussiates, naphthenates and stearates), complexes, and other organic compounds of the metallic elements. Ligands constituting the complexes include OH (hydroxo), alkoxy (e.g., methoxy, ethoxy, propoxy, and butoxy), acyl (e.g., acetyl and propionyl), alkoxycarbonyl (e.g., methoxycarbonyl and ethoxycarbonyl), acetylacetonato, cyclopentadienyl group, halogen atoms (e.g., chlorine and bromine), CO, CN, oxygen atom, $H_2O$ (aquo), phosphines (triphenylphosphine and other triarylphosphines) and other phosphorus compounds, $NH_3$ (ammine), NO, $NO_2$ (nitro), $NO_3$ (nitrato), ethylenediamine, diethylenetriamine, pyridine, phenanthroline and other nitrogen-containing compounds.

Examples of the metallic compounds include, by taking cobalt compounds as an example, cobalt hydroxide, cobalt oxide, cobalt chloride, cobalt bromide, cobalt nitrate, cobalt sulfate, cobalt phosphate, and other inorganic compounds; cobalt acetate, cobalt naphthenate, cobalt stearate, and other salts of organic acids; acetylacetonatocobalt, and other complexes, and other divalent or trivalent cobalt compounds. Illustrative vanadium compounds include, but are not limited to, vanadium hydroxide, vanadium oxide, vanadium chloride, vanadyl chloride, vanadium sulfate, vanadyl sulfate, sodium vanadate, and other inorganic compounds; acetylacetonatovanadium, vanadyl acetylacetonato, and other complexes, and other vanadium compounds having a valence of from 2 to 5. Examples of compounds of the other metallic elements include compounds corresponding to the above-mentioned cobalt or vanadium compounds. Each of these metallic compounds can be used alone or in combination. Specifically, the combination use of a cobalt compound with a manganese compound significantly increases the reaction rate in many cases. The combination use of plural types of metallic compounds having different valances (e.g., a divalent metallic compound in combination with a trivalent metallic compound) is also preferred.

The amount of the metallic compound is, for example, from about 0.001 to about 10 moles and preferably from about 0.005 to about 3 moles relative to 1 mole of the cyclic imide compound, and is, for example, from about 0.00001% to about 10% by mole and preferably from about 0.2% to about 2% by mole relative to 1 mole of the reactant (substrate).

The promoters for use in the present invention also include organic salts each composed of a polyatomic cation or a polyatomic anion and its counter ion, which polyatomic cation or anion contains a Group 15 or Group 16 element of the Periodic Table of Elements having at least one organic group bonded thereto. By using the organic salts as the promoters, the rate and selectivity of the reaction can further be improved.

In the organic salts, the Group 15 elements of the Periodic Table of Elements include N, P, As, Sb and Bi, and the Group 16 elements of the Periodic Table of Elements include, for example, O, S, Se and Te. Preferred elements are N, P, As, Sb and S, of which N, P and S are typically preferred.

The organic groups to be combined with atoms of the elements include, but are not limited to, hydrocarbon groups which may have a substituent, and substituted oxy groups. Such hydrocarbon groups include, but are not limited to, methyl, ethyl, propyl, isopropyl, butyl, isobutyl, s-butyl, t-butyl, pentyl, hexyl, octyl, decyl, tetradecyl, hexadecyl, octadecyl, allyl, and other straight- or branched-chain aliphatic hydrocarbon groups (alkyl groups, alkenyl groups and alkynyl groups) each having from about 1 to about 30 carbon atoms (preferably from about 1 to about 20 carbon atoms); cyclopentyl, cyclohexyl, and other alicyclic hydrocarbon groups each having from about 3 to about 8 carbon atoms; and phenyl, naphthyl, and other aromatic hydrocarbon groups each having from about 6 to about 14 carbon atoms. Substituents which the hydrocarbon groups may have include, but are not limited to, halogen atoms, oxo group, hydroxyl group, substituted oxy groups (e.g., alkoxy groups, aryloxy groups and acyloxy groups), carboxyl group, substituted oxycarbonyl groups, substituted or unsubstituted carbamoyl groups, cyano group, nitro group, substituted or unsubstituted amino groups, alkyl groups (e.g., methyl, ethyl, and other $C_1$-$C_4$ alkyl groups), cycloalkyl groups, aryl groups (e.g., phenyl and naphthyl groups) and heterocyclic groups. The preferred hydrocarbon groups include, for example, alkyl groups each having from about 1 to about 30 carbon atoms and aromatic hydrocarbon groups (especially, phenyl or naphthyl group) each having from about 6 to about 14 carbon atoms. The substituted oxy groups include, for example, alkoxy groups, aryloxy groups and aralkyloxy groups.

Examples of the organic salts include organic ammonium salts, organic phosphonium salts, organic sulfonium salts, and other organic onium salts. Such organic ammonium salts include tetramethylammonium chloride, tetraethylammonium chloride, tetrabutylammonium chloride, tetrahexylammonium chloride, trioctylmethylammonium chloride, triethylphenylammonium chloride, tributyl(hexadecyl) ammonium chloride, di(octadecyl)dimethylammonium chloride, and other quaternary ammonium chlorides, corresponding quaternary ammonium bromides, and other quaternary ammonium salts each having four hydrocarbon groups combined with a nitrogen atom; dimethylpiperidinium chloride, hexadecylpyridinium chloride, methylquinolinium chloride, and other cyclic quaternary ammonium salts. Examples of the organic phosphonium salts include tetramethylphosphonium chloride, tetrabutylphosphonium chloride, tributyl(hexadecyl)phosphonium chloride, triethylphenylphosphonium chloride, and other quaternary phosphonium chlorides, corresponding quaternary phosphonium bromides, and other quaternary phosphonium salts each having four hydrocarbon groups combined with a phosphorus atom. Examples of the organic sulfonium salts include triethylsulfonium iodide, ethyldiphenylsulfonium iodide, and other sulfonium salts each having three hydrocarbon groups combined with a sulfur atom.

The organic salts also include methanesulfonates, ethanesulfonates, octanesulfonates, dodecanesulfonates, and other alkyl-sulfonates (e.g., $C_6$-$C_{18}$ alkyl-sulfonates); benzenesulfonates, p-toluenesulfonates, naphthalenesulfonates, decylbenzenesulfonates, dodecylbenzenesulfonates, and other aryl-sulfonates which may be substituted with an alkyl group (e.g., $C_6$-$C_{18}$ alkyl-arylsulfonates); sulfonic acid type ion exchange resins (ion exchangers); and phosphonic acid type ion exchange resins (ion exchangers).

The amount of the organic salt is, for example, from about 0.001 to about 0.1 mole and preferably from about 0.005 to about 0.08 mole, relative to 1 mole of the cyclic imide compound.

The promoters for use in the present invention also include strong acids (e.g., compounds each having a pKa of less than or equal to 2 at 25° C.). Preferred strong acids include, for example, hydrogen halides, hydrohalogenic acids, sulfuric acid and heteropolyacids. The amount of the strong acid is, for example, from about 0.001 to about 3 moles relative to 1 mole of the cyclic imide compound.

The promoters for use in the present invention also include compounds each having a carbonyl group combined with an electron attractive group. Such compounds each having a carbonyl group combined with an electron attractive group include, for example, hexafluoroacetone, trifluoroacetic acid, pentafluorophenyl methyl ketone, pentafluorophenyl trifluoromethyl ketone and benzoic acid. The amount of these compounds is, for example, from about 0.0001 to about 3 moles relative to 1 mole of the reactant (substrate).

The reaction system in the present invention may include a radical generator or a radical reaction accelerator. Such components include, but are not limited to, halogens (e.g., chlorine and bromine), peracids (e.g., peracetic acid and m-chloroperbenzoic acid), peroxides (e.g., hydrogen peroxide, t-butyl hydroperoxide (TBHP), and other hydroperoxides), nitric acid, nitrous acid or salts thereof, nitrogen dioxide, benzaldehyde and other aldehydes. Such a component in the system may enhance the reaction in some cases. The amount of the aforementioned component is, for example, from about 0.001 to about 1 mole relative to 1 mole of the cyclic imide compound.

The catalysts of the present invention are useful as, for example, radical reaction catalysts. The catalysts of the present invention exhibit similar catalytic activities with those of the conventional N-hydroxyphthalimide catalyst, are highly soluble in fats or oils than N-hydroxyphthalimide and therefore can easily be solved in low-polar substrates or solvents. They can exhibit high catalytic activities in small amounts in reactions of low polar substrates in the absence of solvents or in reactions of substrates in the presence of low-polar solvents. In addition, they can be used in reactions in the absence of solvents and can therefore markedly improve the reaction rate as compared with imide compounds having relatively high hydrophilicity, such as N-hydroxyphthalimide (SP: 33.4).

Examples of reactions, in which the catalysts of the present invention exhibit catalytic activities, include reactions described in the following literature relating to the catalysts such as N-hydroxyphthalimide: Japanese Unexamined Patent Application Publications No. 8-38909, No. 9-327626, No. 10-286467, No. 10-316610, No. 10-309469, No. 10-316625, No. 11-239730, No. 10-310543, No. 11-49764, No. 11-106377, No. 11-226416, No. 11-228484, No. 11-228481, No. 11-315036, No. 11-300212, No. 11-335304, No. 2000-212116, No. 2000-219650, No. 2000-219652 and No. 2000-256304, PCT International Publications No. WO 99/50204, No. WO 00/35835, No. WO 00/46145 and No. WO 00/61665, Japanese Patent Applications No. 11-136339, No. 11-254977, No. 11-372177, No. 2000-648, No. 2000-58054, No. 2000-67682, No. 2000-67679, No. 2000-67680, No. 2000-157356, No. 2000-176494, No. 2000-179185, No. 2000-209205, No. 2000-345822, No. 2000-345823 and No. 2000-345824.

For example, (A) a compound capable of forming a radical is allowed to react with (B) a radical scavenging compound in the presence of the catalyst of the present invention and thereby yields an addition or substitution reaction product between the compound (A) and the compound (B) or a derivative thereof.

Compounds (A) Capable of Forming Radicals

Such compounds (A) capable of forming a radical are not specifically limited, as long as they can form a stable radical, and include, for example, (A1) heteroatom-containing compounds each having a carbon-hydrogen bond at the adjacent position to the heteroatom, (A2) compounds each having a carbon-heteroatom double bond, (A3) compounds each having a methine carbon atom, (A4) compounds each having a carbon-hydrogen bond at the adjacent position to an unsaturated bond, (A5) non-aromatic cyclic hydrocarbons, (A6) conjugated compounds, (A7) amines, (A8) aromatic compounds, (A9) straight-chain alkanes and (A10) olefins.

These compounds may have substituents within ranges not adversely affecting the reaction. Such substituents include, but are not limited to, halogen atoms, hydroxyl group, mercapto group, oxo group, substituted oxy groups (e.g., alkoxy groups, aryloxy groups and acyloxy groups), substituted thio groups, carboxyl group, substituted oxycarbonyl groups, substituted or unsubstituted carbamoyl groups, cyano group, nitro group, substituted or unsubstituted amino groups, sulfo group, alkyl groups, alkenyl group, alkynyl groups, alicyclic hydrocarbon groups, aromatic hydrocarbon groups and heterocyclic groups.

The compounds (A) capable of forming a radical act as radical donative compounds in the reaction.

The heteroatom-containing compounds (A1) each having a carbon-hydrogen bond at the adjacent position to the heteroatom include, for example, (A1-1) primary or secondary alcohols or primary or secondary thiols, (A1-2) ethers each having a carbon-hydrogen bond at the adjacent position to an oxygen atom, or sulfides each having a carbon-hydrogen bond at the adjacent position to a sulfur atom, (A1-3) acetals (including hemiacetals) each having a carbon-hydrogen bond at the adjacent position to an oxygen atom, or thioacetals (including thiohemiacetals) each having a carbon-hydrogen bond at the adjacent position to a sulfur atom.

The primary or secondary alcohols in the compounds (A1-1) include a wide variety of alcohols. These alcohols may be whichever of monohydric, dihydric and polyhydric alcohols.

Such primary alcohols include, but are not limited to, methanol, ethanol, 1-propanol, 1-butanol, 2-methyl-1-propanol, 1-pentanol, 1-hexanol, 1-octanol, 1-decanol, 1-hexadecanol, 2-buten-1-ol, ethylene glycol, trimethylene glycol, hexamethylene glycol, pentaerythritol, and other saturated or unsaturated aliphatic primary alcohols each having from about 1 to about 30 (preferably from about 1 to about 20, and more preferably from about 1 to about 15) carbon atoms; cyclopentylmethyl alcohol, cyclohexylmethyl alcohol, 2-cyclohexylethyl alcohol, and other saturated or unsaturated alicyclic primary alcohols; benzyl alcohol, 2-phenylethyl alcohol, 3-phenylpropyl alcohol, cinnamyl alcohol, and other aromatic primary alcohols; and 2-hydroxymethylpyridine, and other heterocyclic alcohols.

Typical secondary alcohols include, but are not limited to, 2-propanol, s-butyl alcohol, 2-pentanol, 3-pentanol, 3,3-dimethyl-2-butanol, 2-octanol, 4-decanol, 2-hexadecanol, 2-penten-4-ol, 1,2-propanediol, 2,3-butanediol, 2,3-pentanediol, other vicinal diols, and other saturated or unsaturated aliphatic secondary alcohols each having from about 3 to about 30 (preferably from about 3 to about 20, and more preferably from about 3 to about 15) carbon atoms; 1-cyclopentylethanol, 1-cyclohexylethanol, and other secondary alcohols each having an aliphatic hydrocarbon group and an alicyclic hydrocarbon group (e.g., a cycloalkyl group) combined with a carbon atom that is combined with a hydroxyl group; cyclobutanol, cyclopentanol, cyclohexanol, cyclooctanol, cyclododecanol, 2-cyclohexen-1-ol, 2-adamantanol, 2-adamantanols each having from one to four hydroxyl groups at the bridgehead positions, 2-adamantanols each having an oxo group on an adamantane ring, and other saturated or unsaturated alicyclic secondary alcohols (including bridged cyclic secondary alcohols) each having from about 3 to about 20 members (preferably from about 3 to about 15 members, more preferably from about 5 to about 15 members, and typically from about 5 to about 8 members); 1-phenylethanol, 1-phenylpropanol, 1-phenylmethylethanol, diphenylmethanol, and other aromatic secondary alcohols; and 1-(2-pyridyl)ethanol, and other heterocyclic secondary alcohols.

Illustrative alcohols further include, for example, 1-adamantanemethanol, α-methyl-1-adamantanemethanol, α-ethyl-1-adamantanemethanol, α-isopropyl-1-adamantanemethanol, 3-hydroxy-α-methyl-1-adamantanemethanol, 3-carboxy-α-methyl-1-adamantanemethanol, α-methyl-3a-perhydroindenemethanol, α-methyl-4a-decalinmethanol, 8a-hydroxy-α-methyl-4a-decalinmethanol, α-methyl-4a-perhydrofluorenemethanol, α-methyl-4a-perhydroanthracenemethanol, α-methyl-8a-perhydrophenanthrenemethanol, α-methyl-2-tricyclo[5.2.1.0$^{2,6}$]decanemethanol, 6-hydroxy-α-methyl-2-tricyclo[5.2.1.0$^{2,6}$]decanemethanol, α-methyl-2a-perhydroacenaphthenemethanol, α-methyl-3a-perhydrophenalenemethanol, α-methyl-1-norbornanemethanol, α-methyl-2-norbornene-1-methanol, and other alcohols each having a bridged cyclic hydrocarbon group, such as compounds each having a bridged cyclic hydrocarbon group combined with a carbon atom that is combined with a hydroxyl group.

Preferred alcohols include secondary alcohols and the alcohols each having a bridged cyclic hydrocarbon group. Such preferred secondary alcohols include 2-propanol, s-butyl alcohol, and other aliphatic secondary alcohols; 1-cyclohexylethanol, and other secondary alcohols each having an aliphatic hydrocarbon group (e.g., a $C_1$-$C_4$ alkyl group or a $C_6$-$C_{14}$ aryl group) and a non-aromatic carbocyclic group (e.g., a $C_3$-$C_{15}$ cycloalkyl group or a cycloalkenyl group) combined with a carbon atom that is combined with a hydroxyl group; cyclopentanol, cyclohexanol, 2-adamantanol, and other alicyclic secondary alcohols each having from about 3 to about 15 members; 1-phenylethanol, and other aromatic secondary alcohols.

The primary or secondary thiols in the compounds (A1-1) include thiols corresponding to the primary or secondary alcohols.

The ethers each having a carbon-hydrogen bond at the adjacent position to an oxygen atom in the compounds (A1-2) include, but are not limited to, dimethyl ether, diethyl ether, dipropyl ether, diisopropyl ether, dibutyl ether, methyl ethyl ether, methyl butyl ether, ethyl butyl ether, diallyl ether, methyl vinyl ether, ethyl allyl ether, and other aliphatic ethers; anisole, phenetole, dibenzyl ether, phenyl benzyl ether, and other aromatic ethers; and dihydrofuran, tetrahydrofuran, pyran, dihydropyran, tetrahydropyran, morpholine, chroman, isochroman, and other cyclic ethers with which an aromatic or non-aromatic ring may be condensed.

The sulfides each having a carbon-hydrogen bond at the adjacent position to a sulfur atom in the compounds (A1-2) include sulfides corresponding to the aforementioned ethers each having a carbon-hydrogen bond at the adjacent position to an oxygen atom.

The acetals each having a carbon-hydrogen bond at the adjacent position to an oxygen atom in the compounds (A1-3) include, for example, acetals derived from aldehydes and alcohols or acid anhydrides. Such acetals include cyclic acetals and acyclic acetals. The aldehydes include, but are not limited to, formaldehyde, acetaldehyde, propionaldehyde, butyraldehyde, isobutyraldehyde, pentanal, hexanal, decanal, and other aliphatic aldehydes; cyclopentanecarbaldehyde, cyclohexanecarbaldehyde, and other alicyclic aldehydes; benzaldehyde, phenylacetaldehyde, and other aromatic aldehydes. The alcohols include, but are not limited to, methanol, ethanol, 1-propanol, 1-butanol, benzyl alcohol, and other monohydric alcohols; ethylene glycol, propylene glycol, 1,3-propanediol, 2,2-dibromo-1,3-propanediol, and other dihydric alcohols. Typical acetals are, for example, 1,3-dioxolane, 2-methyl-1,3-dioxolane, 2-ethyl-1,3-dioxolane, and other 1,3-dioxolane compounds; 2-methyl-1,3-dioxane, and other 1,3-dioxane compounds; acetaldehyde dimethyl acetal, and other dialkyl acetal compounds.

The thioacetals each having a carbon-hydrogen bond at the adjacent position to a sulfur atom in the compounds (A1-3) include thioacetals corresponding to the aforementioned acetals each having a carbon-hydrogen bond at the adjacent position to an oxygen atom.

The compounds (A2) each having a carbon-heteroatom double bond include, for example, (A2-1) compounds each containing a carbonyl group, (A2-2) compounds each containing a thiocarbonyl group, and (A2-3) imines. The compounds (A2-1) each containing a carbonyl group include ketones and aldehydes. Such ketones and aldehydes include, but are not limited to, acetone, methyl ethyl ketone, methyl isopropyl ketone, methyl isobutyl ketone, methyl s-butyl ketone, methyl t-butyl ketone, 3-pentanone, methyl decyl ketone, methyl isopropyl ketone, isopropyl butyl ketone, methyl vinyl ketone, methyl isopropenyl ketone, methyl cyclohexyl ketone, acetophenone, methyl 2-methylphenyl ketone, methyl 2-pyridyl ketone, cyclohexyl phenyl ketone, and other chain ketones; cyclopropanone, cyclobutanone, cyclopentanone, cyclohexanone, 4-methylcyclohexanone, 4-chlorocyclohexanone, isophorone, cycloheptanone, cyclooctanone, cyclodecanone, cyclododecanone, cyclopentadecanone, 1,3-cyclohexanedione, 1,4-cyclohexanedione, 1,4-cyclooctanedione, 2,2-bis(4-oxocyclohexyl)propane, bis (4-oxocyclohexyl)methane, 4-(4-oxocyclohexyl)cyclohexanone, 2-adamantanone, and other cyclic ketones; biacetyl (2,3-butanedione), 2,3-pentanedione, 3,4-hexanedione, bibenzoyl (benzil), acetylbenzoyl, cyclopentane-1,2-dione, cyclohexane-1,2-dione, and other 1,2-dicarbonyl compounds (e.g., α-diketones); acetoin, benzoin, and other α-keto-alcohols; acetaldehyde, propionaldehyde, butanal, hexanal, succinaldehyde, glutaraldehyde, adipaldehyde, and other aliphatic aldehydes; cyclohexyl aldehyde, citral, citronellal, and other alicyclic aldehydes; benzaldehyde, carboxybenzaldehyde, nitrobenzaldehyde, cinnamaldehyde, salicylaldehyde, anisaldehyde, phthalaldehyde, isophthalaldehyde, terephthalaldehyde, and other aromatic aldehydes; and furfural, nicotinaldehyde, and other heterocyclic aldehydes.

The compounds (A2-2) each having a thiocarbonyl group include compounds each having a thiocarbonyl group corresponding to the compounds (A2-1) each having a carbonyl group.

The imines (A2-3) include, but are not limited to, imines (including oximes and hydrazones) derived from ammonia or amines and the compounds (A2-1) each having a carbonyl group. Such amines include, for example, methylamine, ethylamine, propylamine, butylamine, hexylamine, benzylamine, cyclohexylamine, aniline, and other amines; hydroxylamine, O-methylhydroxylamine, and other hydroxylamines; hydrazine, methylhydrazine, phenylhydrazine, and other hydrazines.

The compounds (A3) each having a methine carbon atom include, for example, (A3-1) cyclic compounds each having a methine group (i.e., a methine carbon-hydrogen bond) as a constitutional unit of its ring and (A3-2) chain compounds each having a methine carbon atom.

The cyclic compounds (A3-1) include, for example, (A3-1a) bridged cyclic compounds each having at least one methine group and (A3-1b) non-aromatic cyclic compounds (e.g., alicyclic hydrocarbons) each having a hydrocarbon group combined with its ring. The bridged cyclic compounds also include compounds each containing two rings commonly possessing two carbon atoms, such as hydrogenated products of condensed polycyclic aromatic hydrocarbons.

The bridged cyclic compounds (A3-1a) include, but are not limited to, decalin, bicyclo[2.2.0]hexane, bicyclo[2.2.2] octane, bicyclo[3.2.1]octane, bicyclo[4.3.2]undecane, bicyclo[3.3.3]undecane, thujone, carane, pinane, pinene, bornane, bornylene, norbornane, norbornene, camphor, camphoric acid, camphene, tricyclene, tricyclo[5.2.1.0$^{3,8}$] decane, tricyclo[4.2.1.1$^{2,5}$]decane, exotricyclo[5.2.1.0$^{2,6}$] decane, endotricyclo[5.2.1.0$^{2,6}$]decane, tricyclo[4.3.1.1$^{2,5}$] undecane, tricyclo[4.2.2.1$^{2,5}$]undecane, endotricyclo [5.2.2.0$^{2,6}$]undecane, adamantane, 1-adamantanol, 1-chloroadamantane, 1-methyladamantane, 1,3-dimethyladamantane, 1-methoxyadamantane, 1-carboxyadamantane, 1-methoxycarbonyladamantane, 1-nitroadamantane, tetracyclo[4.4.0.1$^{2,5}$.1$^{7,10}$]dodecane, perhydroanthracene, perhydroacenaphthene, perhydrophenanthrene, perhydrophenalene, perhydroindene, quinuclidine, and other bridged cyclic hydrocarbons or bridged heterocyclic compounds each having two to four rings, and derivatives thereof. These bridged cyclic compounds each have a methine carbon atom at a bridgehead position (corresponding to a junction position when two rings commonly possess two atoms).

The non-aromatic cyclic compounds (A3-1b) each having a hydrocarbon group combined with its ring include, but are not limited to, 1-methylcyclopentane, 1-methylcyclohexane, limonene, menthene, menthol, carbomenthone, menthone, and other alicyclic hydrocarbons each having from about 3 to about 15 members and having a hydrocarbon group (e.g., an alkyl group) combined with its ring, and their derivatives. The hydrocarbon group just mentioned above may contain from about 1 to about 20 (preferably from about 1 to about 10) carbon atoms The non-aromatic cyclic compounds (A3-1b) each having a hydrocarbon group combined with its ring each have a methine carbon atom at the bonding position between the ring and the hydrocarbon group.

The chain compounds (A3-2) each having a methine carbon atom include, but are not limited to, chain hydrocarbons each having a tertiary carbon atom, such as isobutane, isopentane, isohexane, 3-methylpentane, 2,3-dimethylbutane, 2-methylhexane, 3-methylhexane, 3,4-dimethylhexane, 3-methyloctane, and other aliphatic hydrocarbons each having from about 4 to about 20 (preferably from about 4 to about 10) carbon atoms, and derivatives thereof.

The compounds (A4) each having a carbon-hydrogen bond at the adjacent position to an unsaturated bond include, for example, aromatic compounds each having a methyl group or methylene group at the adjacent position to an aromatic ring (a "benzylic position") and (A4-2) non-aromatic compounds each having a methyl group or methylene group at the adjacent position to an unsaturated bond (e.g., a carbon-carbon triple bond or a carbon-oxygen double bond).

In the aromatic compounds (A4-1), the aromatic ring may be whichever of an aromatic hydrocarbon ring or an aromatic heterocyclic ring. Such aromatic hydrocarbon rings include, but are not limited to, benzene ring, condensed carbocyclic rings (e.g., naphthalene, azulene, indacene, anthracene, phenanthrene, triphenylene, pyrene, and other condensed carbocyclic rings each having condensed two to ten 4- to 7-membered carbocyclic rings). The aromatic heterocyclic rings include, but are not limited to, heterocyclic rings each containing an oxygen atom as a heteroatom (e.g., furan, oxazole, isoxazole, and other 5-membered rings; 4-oxo-4H-pyran and other 6-membered rings; benzofuran, isobenzofuran, 4-oxo-4H-chromene and other condensed rings), heterocyclic rings each containing a sulfur atom as a heteroatom (e.g., thiophene, thiazole, isothiazole, thiadiazole, and other 5-membered rings; 4-oxo-4H-thiopyran and other 6-membered rings; benzothiophene and other condensed rings), heterocyclic rings each containing a nitrogen atom as a heteroatom (e.g., pyrrole, pyrazole, imidazole, triazole, and other 5-membered rings; pyridine, pyridazine, pyrimidine, pyrazine, and other 6-membered rings; indole, quinoline, acridine, naphthyridine, quinazoline, purine, and other condensed rings).

The methylene group at the adjacent position to the aromatic ring may be a methylene group constituting a non-aromatic ring condensed with the aromatic ring. The aromatic compounds (A4-1) may have both methyl group and methylene group at the adjacent position to the aromatic ring.

The aromatic compounds each having a methyl group at the adjacent position to an aromatic ring include, but are not limited to, aromatic hydrocarbons each having from about one to about six methyl groups substituted on the aromatic ring (e.g., toluene, xylene, 1-ethyl-4-methylbenzene, 1-ethyl-3-methylbenzene, 1-isopropyl-4-methylbenzene, 1-t-butyl-4-methylbenzene, 1-methoxy-4-methylbenzene, mesitylene, pseudocumene, durene, methylnaphthalene, dimethylnaphthalene, methylanthracene, 4,4'-dimethylbiphenyl, tolualdehyde, dimethylbenzaldehyde, trimethylbenzaldehyde, toluic acid, trimethylbenzoic acid and dimethylbenzoic acid), and heterocyclic compounds each having from about one to about six methyl groups substituted on a heterocyclic ring (e.g., 2-methylfuran, 3-methylfuran, 3-methythiophene, 2-methylpyridine, 3-methylpyridine, 4-methylpyridine, 2,4-dimethylpyridine, 2,4,6-trimethylpyridine, 4-methylindole, 2-methylquinoline and 3-methylquinoline).

The aromatic compounds each having a methylene group at the adjacent position to an aromatic ring include, but are not limited to, aromatic hydrocarbons each having an alkyl group or substituted alkyl group having two or more carbon atoms (e.g., ethylbenzene, propylbenzene, 1,4-diethylbenzene and diphenylmethane), aromatic heterocyclic compounds each having an alkyl group or substituted alkyl group having two or more carbon atoms (e.g., 2-ethylfuran, 3-propylthiophene, 4-ethylpyridine and 4-butylquinoline), and compounds each having a non-aromatic ring condensed with an aromatic ring, which non-aromatic ring has a methylene group at the adjacent position to the aromatic ring (e.g., dihydronaphthalene, indene, indan, tetralin, fluorene, acenaphthene, phenalene, indanone and xanthene).

The non-aromatic compounds (A4-2) each having a methyl group or methylene group at the adjacent position to an unsaturated bond include, for example, (A4-2a) chain unsaturated hydrocarbons each having a methyl group or methylene group at an "allylic position", and (A4-2b) compounds each having a methyl group or methylene group at the adjacent position to a carbonyl group.

The chain unsaturated hydrocarbons (A4-2a) include, but are not limited to, propylene, 1-butene, 2-butene, 1-pentene, 1-hexene, 2-hexene, 1,5-hexadiene, 1-octene, 3-octene, undecatrines, and other chain unsaturated hydrocarbons each having from about 3 to about 20 carbon atoms. The compounds (A4-2b) include, but are not limited to, ketones (e.g., acetone, methyl ethyl ketone, 3-pentanone, acetophenone, and other chain ketones; and cyclohexanone and other cyclic ketones), carboxylic acids or derivatives thereof (e.g., acetic acid, propionic acid, butanoic acid, pentanoic acid, hexanoic acid, heptanoic acid, phenylacetic acid, malonic acid, succinic acid, glutaric acid, and esters of these acids).

The non-aromatic cyclic hydrocarbons (A5) include (A5-1) cycloalkanes and (A5-2) cycloalkenes.

The cycloalkanes (A5-1) include, but are not limited to, compounds each having a 3- to 30-membered cycloalkane ring, such as cyclopropane, cyclobutane, cyclopentane, cyclohexane, cycloheptane, cyclooctane, cyclononane, cyclodecane, cyclododecane, cyclotetradecane, cyclohexadecane, cyclotetracosane, cyclotriacontane, and derivatives of these compounds. Preferred cycloalkane rings are 5- to 30-membered cycloalkane rings, of which 5- to 20-membered cycloalkane rings are typically preferred.

The cycloalkenes (A5-2) include, but are not limited to, compounds each having a 3- to 30-membered cycloalkene ring, such as cyclopropene, cyclobutene, cyclopentene, cyclooctene, cyclohexene, 1-methyl-cyclohexene, isophorone, cycloheptene and cyclododecene, as well as cyclopentadiene, 1,3-cyclohexadiene, 1,5-cyclooctadiene, and other cycloalkadienes, cyclooctatrienes and other cycloalkatrienes, and derivatives of these compounds. Preferred cyclalkenes include compounds each having a 3- to 20-membered ring, of which compounds each having a 3- to 12-membered ring are typically preferred.

The conjugated compounds (A6) include, for example, (A6-1) conjugated dienes, (A6-2) $\alpha,\beta$-unsaturated nitriles, and (A6-3) $\alpha,\beta$-unsaturated carboxylic acids or derivatives (e.g., esters, amides and acid anhydrides) thereof.

The conjugated dienes (A6-1) include, but are not limited to, butadiene, isoprene, 2-chlorobutadiene and 2-ethylbutadiene. The conjugated dienes (A6-1) also include, herein, vinylacetylene and other compounds each having a double bond and a triple bond conjugated with each other.

The $\alpha,\beta$-unsaturated nitriles (A6-2) include, for example, (meth)acrylonitrile. The $\alpha,\beta$-unsaturated carboxylic acids or derivatives thereof (A6-3) include, but are not limited to, (meth)acrylic acid; methyl (meth)acrylate, ethyl (meth)acrylate, isopropyl (meth)acrylate, butyl (meth)acrylate, 2-hydroxyethyl (meth)acrylate, and other (meth)acrylic esters; (meth)acrylamide, N-methylol (meth)acrylamide, and other (meth)acrylamide derivatives.

The amines (A7) include, but are not limited to, primary or secondary amines such as methylamine, ethylamine, propylamine, butylamine, dimethylamine, diethylamine, dibutylamine, ethylenediamine, 1,4-butanediamine, hydroxylamine, ethanolamine, and other aliphatic amines;

cyclopentylamine, cyclohexylamine, and other alicyclic amines; benzylamine, toluidine, and other aromatic amines; pyrrolidine, piperidine, piperazine, indoline, and other cyclic amines with which an aromatic or non-aromatic ring may be condensed.

The aromatic hydrocarbons (A8) include, but are not limited to, benzene, naphthalene, acenaphthylene, phenanthrene, anthracene, naphthacene, aceanthrylene, triphenylene, pyrene, chrysene, naphthacene, picene, perylene, pentacene, coronene, pyranthrene, ovalene, and other aromatic compounds each having at least one benzene ring. Of these aromatic hydrocarbons, preferred are condensed polycyclic aromatic compounds each having at least a plurality of condensed benzene rings (e.g., two to ten benzene rings). These aromatic hydrocarbons may each have at least one substituent. Examples of such aromatic hydrocarbons each having a substituent are 2-chloronaphthalene, 2-methoxynaphthalene, 1-methylnaphthalene, 2-methylnaphthalene, 2-methylanthracene, 2-t-butylanthracene, 2-carboxyanthracene, 2-ethoxycarbonylanthracene, 2-cyanoanthracene, 2-nitroanthracene and 2-methylpentalene. With each of the benzene rings, a non-aromatic carbon ring, an aromatic heterocyclic ring or a non-aromatic heterocyclic ring may be condensed.

The straight-chain alkanes (A9) include, but are not limited to, methane, ethane, propane, butane, pentane, hexane, heptane, octane, nonane, decane, dodecane, tetradecane, hexadecane, and other straight-chain alkanes each having from about 1 to about 30 carbon atoms, of which straight-chain alkanes each having from about 1 to about 20 carbon atoms are preferred.

The olefins (A10) may be any of α-olefins and internal olefins each of which may have a substituent (e.g., the aforementioned substituents such as hydroxyl group and acyloxy groups) and also include dienes and other olefins each having plural carbon-carbon double bonds. The olefins (A10) include, but are not limited to, ethylene, propylene, 1-butene, 2-butene, isobutene, 1-pentene, 2-pentene, 2,4,4-trimethyl-2-pentene, 1-hexene, 2-hexene, 2,3-dimethyl-2-butene, 3-hexene, 3-hexen-1-ol, 2-hexen-1-ol, 1-octen-3-ol, 1-heptene, 1-octene, 2-octene, 3-octene, 4-octene, 1-nonene, 2-nonene, 1-decene, 1-undecene, 1-dodecene, 1-hexadecene, 1-octadecene, 1,5-hexadiene, 1,6-heptadiene, 1,7-octadiene, 1-acetoxy-3,7-dimethyl-2,6-octadiene, styrene, vinyltoluene, α-methylstyrene, 3-vinylpyridine, 3-vinylthiophene, and other chain olefins; cyclopropene, cyclobutene, cyclopentene, cyclohexene, cycloheptene, cyclooctene, cyclononene, cyclodecene, cycloundecene, cyclododecene, 1,4-cyclohexadiene, 1,4-cycloheptadiene, cyclodecadienes, cyclododecadienes, limonene, 1-p-menthene, 3-p-menthene, carveol, bicyclo[2.2.1]hept-2-ene, bidyclo[3.2.1]oct-2-ene, α-pinene, 2-bornene, and other cyclic olefins.

Each of these compounds capable of forming a radical can be used alone or in combination, and in the latter case, the compounds used in combination may belong to the same or different categories. For example, when two or more types of these compounds, especially two or more types of these compounds belonging to different categories, are used in a reaction with oxygen or another oxygen-atom-containing gas, one of the substrates acts as a co-reacting agent (e.g., co-oxidizing agent) with respect to the other and thereby yields significantly increased reaction rate in some cases.

Radical Scavenging Compounds (B)

The radical scavenging compounds (B) may be any compounds as long as they can form a stable compound as a result of the reaction with a radical. Examples of such compounds include (B1) unsaturated compounds, (B2) compounds each having a methine carbon atom, (B3) heteroatom-containing compounds and (B4) oxygen-atom-containing reacting agents (e.g., oxygen-atom-containing gases). Each of these compounds may be used alone or in combination.

These compounds may have substituents within ranges not adversely affecting the reaction. Such substituents include, but are not limited to, halogen atoms, hydroxyl group, mercapto group, oxo group, substituted oxy groups (e.g., alkoxy groups, aryloxy groups and acyloxy groups), substituted thio groups, carboxyl group, substituted oxycarbonyl groups, substituted or unsubstituted carbamoyl groups, cyano group, nitro group, substituted or unsubstituted amino groups, sulfo group, alkyl groups, alkenyl group, alkynyl groups, alicyclic hydrocarbon groups, aromatic hydrocarbon groups and heterocyclic groups.

The unsaturated compounds (B1) include a wide variety of compounds each having an unsaturated bond. Such compounds include, for example, (B1-1) unsaturated compounds each having an electron attractive group at the adjacent position to a carbon-carbon unsaturated bond [active olefins (electron-deficient olefins) and other active unsaturated compounds], (B1-2) compounds each having a carbon-carbon triple bond, (B1-3) compounds each having an aromatic ring, (B1-4) ketenes, (B1-5) isocyanate or thiocyanate compounds and (B1-6) inert olefins.

The active unsaturated compounds (B1-1) include, but are not limited to, methyl (meth)acrylate, ethyl (meth)acrylate, isopropyl (meth)acrylate, phenyl (meth)acrylate, methyl crotonate, ethyl crotonate, methyl 3-methyl-2-butenoate, ethyl 3-methyl-2-butenoate, methyl 2-pentenoate, ethyl 2-pentenoate, methyl 2-octenoate, ethyl 2-octenoate, methyl cinnamate, ethyl cinnamate, methyl 4,4,4-trifluoro-2-butenoate, ethyl 4,4,4-trifluoro-2-butenoate, dimethyl maleate, diethyl maleate, dimethyl fumarate, diethyl fumarate, methyl 3-cyanoacrylate, ethyl 3-cyanoacrylate, and other α,β-unsaturated esters; vinyl methyl ketone, vinyl ethyl ketone, methyl 1-propenyl ketone, and other α,β-unsaturated ketones; propenal, crotonaldehyde, and other α,β-unsaturated aldehydes; acrylonitrile, methacrylonitrile, and other α,β-unsaturated nitriles; (meth)acrylic acid, crotonic acid, and other α, β-unsaturated carboxylic acids; (meth)acrylamide, and other α,β-unsaturated carboxamides; N-(2-propenylidene)methylamine, N-(2-butenylidene)methylamine, and other α,β-unsaturated imines; styrene, vinyltoluene, α-methylstyrene, β-methylstyrene, other styrene derivatives, and other compounds each having an aryl group bonded at the adjacent position to a carbon-carbon unsaturated bond; butadiene, isoprene, 2-chlorobutadiene, 2-ethylbutadiene, vinylacetylene, cyclopentadiene derivatives, and other conjugated dienes (including compounds having a double bond and a triple bond conjugated with each other).

The compounds (B1-2) each having a carbon-carbon triple bond include, for example, methylacetylene and 1-butyne. The compounds (B1-3) each having an aromatic ring include, for example, compounds each having a benzene ring, a naphthalene ring or another aromatic carbon ring; and compounds each having a pyrrole ring, a furan ring, a thiophene ring or another aromatic heterocyclic ring. The ketenes (B1-4) include, for example, ketene and 2-methylketene. The isocyanate or thiocyanate compounds (B1-5) include, but are not limited to, methyl isocyanate, ethyl isocyanate, phenyl isocyanate, methyl thiocyanate, ethyl thiocyanate and phenyl thiocyanate.

The inert olefins (B1-6) may be whichever of α-olefins and internal olefins and also include dienes and other olefins each having plural carbon-carbon double bonds. Examples of the inert olefins (B1-6) include ethylene, propylene, 1-butene, 2-butene, isobutene, 1-pentene, 2-pentene, 1-hexene, 2-hexene, 3-hexene, 1-heptene, 1-octene, 2-octene, 3-octene, 4-octene, 1-nonene, 1-decene, 1-dodecene, 1,5-hexadiene, 1,6-heptadiene, 1,7-octadiene, and other chain olefins (alkenes); cyclopentene, cyclohexene, cyclooctene, cyclodecene, cyclododecene, and other cyclic olefins (cycloalkenes).

The compounds (B2) each having a methine carbon atom include, for example, the compounds exemplified as the compounds (A3). The one and same compound can be used as the compound (A3) and the compound (B2) in the reaction.

The heteroatom-containing compounds (B3) include, for example, (B3-1) compounds each having a sulfur atom, (B3-2) compounds each having a nitrogen atom, (B3-3) compounds each having a phosphorus atom, and (B3-4) compounds each having an oxygen atom. The compounds (B3-1) each having a sulfur atom include, for example, sulfides and thiols. The compounds (B3-2) each having a nitrogen atom include, for example, amines. The compounds (B3-3) each having a phosphorus atom include, for example, phosphites. The compounds (B3-4) each having an oxygen atom include, for example, N-oxides.

The oxygen-atom-containing reacting agents (B4) include, for example, oxygen-atom-containing gases, nitric acid, nitrous acid or salts thereof (hereinafter referred to as "nitric acids"). The oxygen-atom-containing gases include those each having a boiling point (or sublimation point) of less than or equal to 45° C. Such oxygen-atom-containing gases include, but are not limited to, (B4-1) oxygen, (B4-2) carbon monoxide, (B4-3) nitrogen oxides and (B4-4) sulfur oxides. Each of these oxygen-atom-containing reacting agents can be used alone or in combination.

The oxygen (B4-1) may be any of molecular oxygen and active oxygen. The molecular oxygen is not specifically limited and includes pure oxygen, oxygen diluted with an inert gas such as nitrogen, helium, argon or carbon dioxide gas, and air. Molecular oxygen is often used as the oxygen.

The carbon monoxide (B4-2) may be pure carbon monoxide or carbon monoxide diluted with an inert gas. When carbon monoxide is used in combination with oxygen, a carboxylic acid can be obtained in a high yield as a result of the reaction with the compound (A).

The nitrogen oxides (B4-3) include compounds represented by the following formula: $N_xO_y$, wherein x is 1 or 2; and y is an integer of from 1 to 6. In these compounds, y is generally an integer of from 1 to 3 when x is 1; and y is generally an integer of from 1 to 6 when x is 2.

Examples of the nitrogen oxides are $N_2O$, $NO$, $N_2O_3$, $NO_2$, $N_2O_4$, $N_2O_5$, $NO_3$ and $N_2O_6$. Each of these nitrogen oxides can be used alone or in combination. The nitrogen oxides may be pure substances or mixtures mainly containing nitrogen oxides. Such mixtures mainly containing nitrogen oxides include exhausted gases formed in oxidation processes with nitric acid.

Preferred nitrogen oxides include, for example, $NO$, $N_2O_3$, $NO_2$ and $N_2O_5$. In this connection, $N_2O_3$ can easily be obtained upon a reaction of dinitrogen monoxide ($N_2O$) and/or nitrogen monoxide (NO) with oxygen. More specifically, $N_2O_3$ can be prepared by introducing dinitrogen monoxide (or nitrogen monoxide) and oxygen into a cooled reactor to yield a blue liquid $N_2O_3$. Accordingly, the reaction according to the present invention can be performed by introducing dinitrogen monoxide ($N_2O$) and/or nitrogen monoxide (NO) and oxygen into a reaction system without the previous formation of $N_2O_3$. The nitrogen oxides can be used in combination with oxygen. For example, by using $NO_2$ in combination with oxygen, the yield of the product (e.g., a nitro compound) can further be improved.

The sulfur oxides (B4-4) include compounds represented by the following formula: $S_pO_q$, wherein p is 1 or 2; and q is an integer of from 1 to 7. In these compounds, q is generally an integer of from 1 to 4 when p is 1; and q is generally 3 or 7 when p is 2.

Such sulfur oxides include, but are not limited to, SO, $S_2O_3$, $SO_2$, $SO_3$, $S_2O_7$ and $SO_4$. Each of these sulfur oxides can be used alone or in combination. Fuming sulfuric acid containing sulfur trioxide can be employed as the sulfur trioxide.

Preferred sulfur oxides include those mainly containing at least one of sulfur dioxide ($SO_2$) and sulfur trioxide ($SO_3$). The sulfur oxide can be used in combination with oxygen. For example, by using sulfur dioxide ($SO_2$) in combination with oxygen, a corresponding sulfonic acid can be obtained in a high yield as a result of the reaction with the compound (A).

The salts of nitric acid or nitrous acid include, but are not limited to, sodium salts, potassium salts, and other alkali metal salts; magnesium salts, calcium salts, barium salts, and other alkaline earth metal salts; silver salts, aluminium salts, zinc salts, and salts of other metals. Preferred salts include alkali metal salts of nitric acid or nitrous acid.

The nitric acids can be supplied as intact to the reaction system or may be supplied in the form of solutions such as aqueous solutions. Alternatively, these components may be formed in the reaction system and may be subjected to the reaction.

The reaction between the compound (A) capable of forming a radical and the radical scavenging compound (B) is performed in the presence of, or in the absence of, a solvent. Such solvents include, but are not limited to, acetic acid, propionic acid, and other organic acids; acetonitrile, propionitrile, benzonitrile, and other nitrites; formamide, acetamide, dimethylformamide (DMF), dimethylacetamide, and other amides; hexane, octane, and other aliphatic hydrocarbons; chloroform, dichloromethane, dichloroethane, carbon tetrachloride, chlorobenzene, trifluoromethylbenzene, and other halogenated hydrocarbons; nitrobenzene, nitromethane, nitroethane, and other nitro compounds; ethyl acetate, butyl acetate, and other esters; and mixtures of these solvents. The catalysts of the present invention are highly soluble in oils or fats and can advantageously be used in reactions in the absence of solvents or in the presence of low-polar solvents.

The ratio of the compound (A) capable of forming a radical to the radical scavenging compound (B) can appropriately be set depending on the types (costs, reactivities) of the two compounds or combinations thereof. For example, the compound (A) may be used in excess (e.g., from about 2 to about 50 times by mole) to the compound (B). Alternatively, the compound (B) may be used in excess to the compound (A).

The process of the present invention can smoothly proceed reactions under mild conditions. A reaction temperature can appropriately be set depending on the types of the compound (A) and compound (B) or the type of the target product, and is, for example, from about 0° C. to about 300° C., and preferably from about 20° C. to about 200° C. The reaction can be performed at atmospheric pressure or under a pressure (under a load). When the reaction is performed under a pressure, the pressure is usually from about 0.1 to about 10 MPa (e.g., from about 0.15 to about 8 MPa, and particularly from about 1 to about 8 MPa). A reaction time can appropriately be set within a range of, for example, from about 10 minutes to about 48 hours depending on the reaction temperature and pressure.

The reaction can be performed in a batch system, semi-batch system, continuous system or another conventional system. By adding the cyclic imide compound catalyst to the reaction system in installments, the target compound can be obtained with a higher conversion or selectivity in many cases.

After the completion of the reaction, reaction products can be separated and purified by techniques such as filtration, concentration, distillation, extraction, crystallization, recrystallization, column chromatography, and other separation means, or any combination of these separation means.

The process of the present invention yields an addition or substitution reaction product or a derivative thereof depending on the combination of the compound (A) capable of forming a radical and the radical scavenging compound (B). Such addition or substitution reaction products include, for example, carbon-carbon bonded products (e.g., coupling reaction products), oxidation products, carboxylation products, nitration products and sulfonation products.

For example, when the heteroatom-containing compound (A1) having a carbon-hydrogen bond at the adjacent position to the heteroatom is used as the compound (A), the adjacent position to the heteroatom is combined with an atom (e.g. a carbon atom) constituting an unsaturated bond of the unsaturated compound (B1), to the methine carbon atom of the compound (B2) having a methine carbon atom, or to the heteroatom of the heteroatom-containing compound (B3) and thereby yields an addition or substitution reaction product or a derivative thereof.

When the compound (A2) having a carbon-heteroatom double bond (e.g., the carbonyl-group-containing compound)is used as the compound (A), a bond between a carbon atom relating to the carbon-heteroatom double bond (e.g., a carbonyl carbon atom) and an atom adjacent to the carbon atom is broken, and an atomic group containing the carbon-heteroatom double bond (e.g., an acyl group) is combined with the aforementioned position of the compound (B1), (B2) or (B3) to yield an addition or substitution reaction product or a derivative thereof.

When the compound (A3) having a methine carbon atom is used as the compound (A), the methine carbon atom is combined with the aforementioned position of the compound (B1), (B2) or (B3) to yield an addition or substitution reaction product or a derivative thereof.

Generally, the use of the unsaturated compound (B1) as the radical scavenging compound (B) yields an addition reaction product, and the use of the compound (B2) having a methine carbon atom as the compound (B) yields a substitution reaction product (e.g., a coupling product).

The reaction between the oxygen-atom-containing reacting agent (B4) as the radical scavenging compound (B) with the compound (A) yields an organic compound having an oxygen-atom-containing group (e.g., hydroxyl group, oxo group, carboxyl group, nitro group or sulfur acid group) depending on the type of the oxygen-atom-containing reacting agent.

By using two or more types of the compounds (A) capable of forming a radical and/or the radical scavenging compounds (B) and thereby inviting sequential addition or substitution reactions, a complicated organic compound can be obtained through one step according to the process of the present invention. For example, when the unsaturated compound (B1) and oxygen (B4-1) as the radical scavenging compounds (B) are allowed to react with the compound (A), a group derived from the compound (A) is combined with one of the two carbon atoms constituting the unsaturated bond as mentioned above, and a hydroxyl group derived from the oxygen is introduced into the other carbon atom.

A reaction mechanism in the process of the present invention is not yet clarified in detail but is supposed as follows. During the reaction, an oxidized active species [e.g., imido-N-oxy radical (>NO•)] is formed as in the cases using N-hydroxyphthalimide as a catalyst, the oxidized active species withdraws a hydrogen from the compound (A) and allows the compound (A) to form a radical, for example, at the carbon atom at the adjacent position to the heteroatom in the compound (A1), at the carbon atom relating to the carbon-heteroatom double bond in the compound (A2), at the methine carbon atom in the compound (A3), or at the carbon atom at the adjacent position to the unsaturated bond in the compound (A4); the thus-formed radical reacts with the compound (B) and thereby yields a corresponding addition or substitution reaction product.

The above-formed addition or substitution reaction product may further undergo, for example, dehydration reaction, cyclization reaction, decarboxylation reaction, rearrangement reaction or isomerization reaction in the reaction system depending on the structure thereof or reaction conditions and thereby yields a corresponding derivative.

The reaction between the compound (A) capable of forming a radical and the radical scavenging compound (B) should preferably be performed under conditions with minimal polymerization inhibitors (e.g., hydroquinone). For example, the proportion of the polymerization inhibitor in the reaction system should preferably be less than or equal to 1000 ppm, and more preferably less than or equal to 100 ppm. If the proportion of the polymerization inhibitor exceeds 1000 ppm, a reaction rate is liable to decrease, and the imide catalyst and/or the promoter has to be used in large amounts in some cases. In contrast, when the proportion of the polymerization inhibitor in the reaction system is low, the reaction rate increases to increase a yield, and the reaction results have a high reproducibility to stably yield a target compound. The unsaturated compounds (B1) or other compounds for use in commercial, to which a polymerization inhibitor is added, should preferably be subjected to elimination of the polymerization inhibitor by, for example, distillation, prior to the reaction. The same goes for any reaction in which the compound (A) is allowed to react with the compound (B) in the presence of the cyclic imide compound.

By using an appropriate combination of the compound (A) capable of forming a radical and the radical scavenging compound (B) in the reaction according to the present invention, a variety of organic compounds as mentioned below can be obtained.

1. Production of 1,3-Dihydroxy Compounds

By catalysis of the cyclic imide compound, an alcohol represented by following Formula (2):

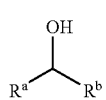

(2)

wherein $R^a$ and $R^b$ are the same or different and are each a hydrogen atom or an organic group, where $R^a$ and $R^b$ may be combined to form a ring with the adjacent carbon atom, is allowed to react with (B4-1) oxygen and (B1-1) an active olefin represented by following Formula (3):

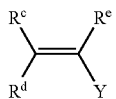

wherein $R^c$, $R^d$ and $R^e$ are the same or different and are each a hydrogen atom or an organic group; and Y is an electron attractive group, where at least two of $R^c$, $R^d$, $R^e$ and Y may be combined to form a ring with the adjacent carbon atom or carbon-carbon bond, and thereby yields a 1,3-dihydroxy compound represented by following Formula (4):

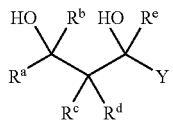

wherein $R^a$, $R^b$, $R^c$, $R^d$, $R^e$ and Y have the same meanings as defined above. This reaction can be performed pursuant to a process described in PCT International Publication Number WO 00/35835 (a process using N-hydroxyphthalimide or another catalyst).

Alcohols

The organic group in $R^a$ and $R^b$ in Formula (2) has only to be an organic group that does not adversely affect the reaction (e.g., an organic group that is not reactive under reaction conditions according to the process). Such organic groups include, for example, hydrocarbon groups and heterocyclic groups.

The hydrocarbon groups include aliphatic hydrocarbon groups, alicyclic hydrocarbon groups and aromatic hydrocarbon groups. Such aliphatic hydrocarbon groups include, but are not limited to, straight- or branched-chain aliphatic hydrocarbon groups (alkyl groups, alkenyl groups and alkynyl groups) each having from about 1 to about 20 carbon atoms. The alicyclic hydrocarbon groups include, but are not limited to, monocyclic alicyclic hydrocarbon groups (e.g., cycloalkyl groups and cycloalkenyl groups) each having from about 3 to about 20 carbon atoms (preferably having from about 3 to about 15 carbon atoms); and bridged cyclic hydrocarbon groups. The aromatic hydrocarbon groups include, for example, aromatic hydrocarbon groups each having from about 6 to about 14 carbon atoms. These hydrocarbon groups may have at least one substituent.

Heterocyclic rings constituting the heterocyclic groups in $R^a$ and $R^b$ include aromatic heterocyclic rings and non-aromatic heterocyclic rings. Such heterocyclic rings include heterocyclic rings each containing an oxygen atom as a heteroatom, heterocyclic rings each containing a sulfur atom as a heteroatom, and heterocyclic rings each containing a nitrogen atom as a heteroatom. These heterocyclic groups may have at least one substituent.

The rings formed by $R^a$ and $R^b$ with the adjacent carbon atom include, but are not limited to, cyclopentane, cyclohexane, cyclododecane, decalin, adamantane, and other non-aromatic carbon rings (cycloalkane rings, cycloalkene rings and bridged carbon rings) each having from about 3 to about 20 members (preferably from about 3 to about 15 members, more preferably from about 5 to about 15 members, and typically from about 5 to about 8 members). These rings may have at least one substituent (e.g., similar groups to the substituents that the hydrocarbon groups may have). With each of these rings, another ring (a non-aromatic ring or an aromatic ring) may be condensed.

Preferred substituent $R^a$ includes hydrogen atom, $C_1$-$C_4$ alkyl groups and $C_6$-$C_{14}$ aryl groups. Preferred $R^b$ includes hydrogen atom, $C_1$-$C_{10}$ aliphatic hydrocarbon groups and alicyclic hydrocarbon groups. Alternatively, $R^a$ and $R^b$ are preferably combined to form a non-aromatic carbon ring having from about 3 to about 15 members (particularly from about 5 to about 8 members) with the adjacent carbon atom.

The alcohols represented by Formula (2) include, for example, those exemplified as the primary or secondary alcohols in compounds (A1-1).

Preferred alcohols include secondary alcohols and alcohols in which the substituent $R^b$ is a bridged cyclic hydrocarbon group. Such preferred secondary alcohols include, for example, 2-propanol, s-butyl alcohol, and other aliphatic secondary alcohols; 1-cyclohexylethanol, and other secondary alcohols each having an aliphatic hydrocarbon group (e.g., a $C_1$-$C_4$ alkyl group or a $C_6$-$C_{14}$ aryl group) and a non-aromatic carbocyclic group (e.g., a $C_3$-$C_{15}$ cycloalkyl group or a cycloalkenyl group) combined with a carbon atom that is combined with a hydroxyl group; cyclopentanol, cyclohexanol, 2-adamantanol, and other alicyclic secondary alcohols each having from about 3 to about 15 members; 1-phenylethanol, and other aromatic secondary alcohols.

Active Olefins

The organic groups in $R^c$, $R^d$ and $R^e$ in the active olefins represented by Formula (3) can be any organic groups, as long as they do not adversely affect the reaction (e.g., organic groups that are not active under reaction conditions according to the process of the present invention). Such organic groups include, but are not limited to, halogen atoms, hydrocarbon groups, heterocyclic groups, substituted oxycarbonyl groups (e.g., alkoxycarbonyl groups, aryloxycarbonyl groups, aralkyloxycarbonyl groups and cycloalkyloxycarbonyl groups), carboxyl group, substituted or unsubstituted carbamoyl groups (N-substituted or unsubstituted amide groups), cyano group, nitro group, sulfur acid radicals (sulfonic acid groups and sulfinic acid groups), sulfur acid ester groups (sulfonic acid ester groups and sulfinic acid ester groups), acyl groups, hydroxyl group, alkoxy groups and N-substituted or unsubstituted amino groups. The carboxyl group, hydroxyl group and amino groups may be protected by conventional protecting groups.

The halogen atoms include fluorine, chlorine, bromine and iodine atoms. The hydrocarbon groups include, for example, the groups exemplified as the hydrocarbon groups in $R^a$ and $R^b$. These hydrocarbon groups may have at least one substituent. The heterocyclic groups include, for example, the groups exemplified as the heterocyclic groups in $R^a$ and $R^b$. These heterocyclic groups may have at least one substituent. The alkoxycarbonyl groups include, but are not limited to, methoxycarbonyl, ethoxycarbonyl, propoxycarbonyl, isopropoxycarbonyl, butoxycarbonyl, t-butoxycarbonyl, and other $C_1$-$C_6$ alkoxy-carbonyl groups. The aryloxycarbonyl groups include, but are not limited to, phenyloxycarbonyl group. The aralkyloxycarbonyl groups include, for example, benzyloxycarbonyl group. Illustrative cycloalkyloxycarbonyl groups are cyclopentyloxycarbonyl and cyclohexyloxycarbonyl groups.

The substituted carbamoyl groups include, for example, N-methylcarbamoyl and N,N-dimethylcarbamoyl groups. Illustrative sulfonic acid ester groups are methyl sulfonate, ethyl sulfonate, and other sulfonic acid $C_1$-$C_4$ alkyl ester groups. Illustrative sulfinic acid ester groups are methyl sulfinate, ethyl sulfinate, and other sulfinic acid $C_1$-$C_4$ alkyl ester groups. The acyl groups include, but are not limited to, acetyl, propionyl, and other aliphatic acyl groups (e.g., $C_2$-$C_7$ aliphatic acyl groups), and benzoyl, and other aromatic acyl groups. The alkoxy groups include, but are not limited to, methoxy, ethoxy, propoxy, butoxy, and other alkoxy groups each having from about 1 to about 6 carbon atoms. The N-substituted amino groups include, for example, N,N-dimethylamino, N,N-diethylamino, and piperidino groups.

Preferred $R^c$, $R^d$, and $R^e$ include, for example, hydrogen atom, hydrocarbon groups [e.g., $C_1$-$C_6$ aliphatic hydrocarbon groups (particularly $C_1$-$C_4$ aliphatic hydrocarbon groups), $C_6$-$C_{14}$ aryl groups (e.g., phenyl group), cycloalkyl groups (e.g., cycloalkyl groups each having from about 3 to about 8 members), haloalkyl groups (e.g., trifluoromethyl group, and other $C_1$-$C_6$ haloalkyl groups, particularly $C_1$-$C_4$ haloalkyl groups)], heterocyclic groups, substituted oxycarbonyl groups (e.g., $C_1$-$C_6$ alkoxy-carbonyl groups, aryloxycarbonyl groups, aralkyloxycarbonyl groups and cycloalkyloxycarbonyl groups), carboxyl group, substituted or unsubstituted carbamoyl groups, cyano group, nitro group, sulfur acid groups, sulfur acid ester groups and acyl groups. Typically preferred $R^c$ and $R^d$ are, for example, hydrogen atom, $C_1$-$C_6$ aliphatic hydrocarbon groups (particularly $C_1$-$C_4$ aliphatic hydrocarbon groups), $C_6$-$C_{14}$ aryl groups (e.g., phenyl group), cycloalkyl groups (e.g., cycloalkyl groups each having from about 3 to about 8 members), haloalkyl groups (e.g., trifluoromethyl group and other $C_1$-$C_6$ haloalkyl groups, particularly $C_1$-$C_4$ haloalkyl groups)], substituted oxycarbonyl groups (e.g., $C_1$-$C_6$ alkoxy-carbonyl groups, aryloxycarbonyl groups, aralkyloxycarbonyl groups and cycloalkyloxycarbonyl groups) and cyano group. Typically preferred Re includes, for example, hydrogen atom and $C_1$-$C_6$ aliphatic hydrocarbon groups (especially, $C_1$-$C_4$ aliphatic hydrocarbon groups).

The rings formed by at least two of $R^c$, $R^d$ and $R^e$ ($R^c$ and $R^d$, $R^c$ and $R^e$, $R^d$ and $R^e$, or $R^c$ and $R^d$ and $R^e$) with the adjacent carbon atom or carbon-carbon bond include cyclopropane, cyclobutane, cyclopentane, cyclopentene, cyclohexane, cyclohexene, cyclooctane, cyclododecane, and other alicyclic carbon rings (e.g., cycloalkane rings and cycloalkene rings) each having from about 3 to about 20 members. These rings may have at least one substituent, and another ring (a non-aromatic ring or an aromatic ring) may be condensed with each of these rings.

The electron attractive groups Y include, but are not limited to, methoxycarbonyl, ethoxycarbonyl, and other alkoxycarbonyl groups; phenoxycarbonyl, and other aryloxycarbonyl groups; formyl, acetyl, propionyl, benzoyl, and other acyl groups; cyano group; carboxyl group; carbamoyl, N,N-dimethylcarbamoyl, and other substituted or unsubstituted carbamoyl groups; —CH═N—R, where R is, for example, an alkyl group; phenyl, naphthyl, and other aryl groups; vinyl, 1-propenyl, ethynyl, and other 1-alkenyl groups or 1-alkynyl groups.

The rings formed by Y and at least one of $R^c$, $R^d$ and $R^e$ with the adjacent carbon atom or carbon-carbon bond include, but are not limited to, cyclopentadiene ring, pyrrole ring, furan ring, and thiophene ring.

Examples of the active olefins represented by Formula (3) include the compounds exemplified as the active unsaturated compounds (B1-1).

Reaction

The reaction of the alcohol represented by Formula (2) with the active olefin represented by Formula (3) and oxygen can be performed in accordance with the procedure described in the reaction between the compound (A) and the compound (B).

In this reaction, the 1,3-dihydroxy compound represented by Formula (4) is supposed to be formed in the following manner. A 1-hydroxyalkyl radical corresponding to the alcohol represented by Formula (2) is formed in the system, attacks and is added to a carbon atom at the beta-position of the group Y between the two carbon atoms constituting an unsaturated bond of the active olefin represented by Formula (3), and oxygen attacks a radical at the alpha-position formed as a result of the addition and thereby yields the 1,3-dihydroxy compound represented by Formula (4).

In the compound represented by Formula (4) formed as a result of the reaction, when Y is a carboxyl group or an ester group such as alkoxycarbonyl group or aryl oxycarbonyl group, a cyclization reaction may further proceed in the system to yield a furanone derivative α-hydroxy-γ-butyrolactone derivative) represented by Formula (6), as described later. The yield of the furanone derivative can be improved by controlling the type and proportion of the promoter or further subjecting the product to aging after the addition reaction (or subsequent oxidation reaction). A reaction temperature in the aging procedure may be set higher than that in the addition reaction. The furanone derivative can also be produced by isolating the compound represented by Formula (4), for example dissolving the isolated compound in a solvent, and heating the solution according to necessity. Such solvents include, but are not limited to, the solvents mentioned later, as well as benzene, toluene, and other aromatic hydrocarbons; cyclohexane and other alicyclic hydrocarbons; acetone, cyclohexanone, and other ketones; diethyl ether, tetrahydrofuran, and other ethers; methanol, ethanol, isopropyl alcohol, and other alcohols. A reaction temperature in this procedure is, for example, from about 0° C. to about 150° C. and preferably from about 30° C. to about 100° C.

2. Production of α-Hydroxy-γ-butyrolactone Derivatives

By catalysis of the cyclic imide compound, the alcohol represented by Formula (2) is allowed to react with (B4-1) oxygen and an α,β-unsaturated carboxylic acid derivative represented by following Formula (5):

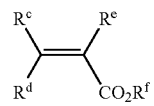

(5)

wherein $R^c$, $R^d$, $R^e$ and $R^f$ are the same or different and are each a hydrogen atom or an organic group, where at least two of $R^c$, $R^d$ and $R^e$ may be combined to form a ring with the adjacent carbon atom or carbon-carbon bond, and thereby yields an α-hydroxy-γ-butyrolactone derivative represented by following Formula (6):

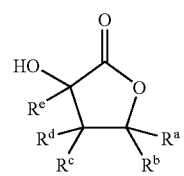

(6)

wherein $R^a$, $R^b$, $R^c$, $R^d$ and $R^e$ have the same meanings as defined above. This reaction can be performed pursuant to the process described in PCT International Publication Number WO 00/35835 (the process using N-hydroxyphthalimide or another catalyst).

Alcohols

The alcohols represented by Formula (2) include similar alcohols to those in the production of the 1,3-dihydroxy compounds.

α,β-Unsaturated Carboxylic Acid Derivatives

The substituents $R^c$, $R^d$ and $R^e$ in Formula (5) are similar to $R^c$, $R^d$ and $R^e$ in Formula (3). Organic groups in $R^f$ include organic groups that do not adversely affect the reaction (e.g., organic groups that are not active under reaction conditions according to the process of the present invention), such as hydrocarbon groups and heterocyclic groups. If the compound represented by Formula (5) has a substituted oxycarbonyl group in addition to —$CO_2R^f$ group indicated in Formula (5), the —$CO_2R^f$ group is involved in a cyclization reaction, but the other substituted oxycarbonyl group can remain as intact in the product. The other substituted oxycarbonyl group is therefore included in the inert organic groups.

When at least one of $R^c$ and $R^d$ is an electron attractive organic group, a target α-hydroxy-γ-butyrolactone derivative can be obtained in a significantly high yield. Such electron attractive organic groups include, for example, haloalkyl groups, substituted oxycarbonyl groups, carboxyl group, substituted or unsubstituted carbamoyl groups, cyano group, nitro group, sulfur acid groups and sulfur acid ester groups.

The substituent $R^f$ is often a hydrogen atom or a hydrocarbon group and is preferably a $C_1$-$C_6$ alkyl group (especially a $C_1$-$C_4$ alkyl group), a $C_2$-$C_6$ alkenyl group (especially a $C_2$-$C_4$ alkenyl group) or a $C_6$-$C_{10}$ aryl group.

Examples of the α,β-unsaturated carboxylic acid derivatives represented by Formula (5) are (meth)acrylic acid; methyl (meth)acrylate, ethyl (meth)acrylate, isopropyl (meth)acrylate, phenyl (meth)acrylate, and other (meth) acrylic esters; crotonic acid; methyl crotonate, ethyl crotonate, and other crotonic esters; 3-methyl-2-butenoic acid; methyl 3-methyl-2-butenoate, ethyl 3-methyl-2-butenoate, and other 3-methyl-2-butenoic esters; 2-pentenoic acid; methyl 2-pentenoate, ethyl 2-pentenoate, and other 2-pentenoic esters; 2-octenoic acid; methyl 2-octenoate, ethyl 2-octenoate, and other 2-octenoic esters; cinnamic acid; methyl cinnamate, ethyl cinnamate, and other cinnamic esters; 4,4,4-trifluoro-2-butenoic acid; methyl 4,4,4-trifluoro-2-butenoate, ethyl 4,4,4-trifluoro-2-butenoate, and other 4,4,4-trifluoro-2-butenoic esters; maleic acid; dimethyl maleate, diethyl maleate, and other maleic esters; fumaric acid; dimethyl fumarate, diethyl fumarate, and other fumaric esters; 3-cyanoacrylic acid; methyl 3-cyanoacrylate, ethyl 3-cyanoacrylate, and other 3-cyanoacrylic esters; and other α,β-unsaturated carboxylic acids each having from about 2 to about 15 carbon atoms or esters thereof (e.g., $C_1$-$C_6$ alkyl esters, $C_2$-$C_6$ alkenyl esters and aryl esters)

Reaction

The reaction of the alcohol represented by Formula (2) with oxygen and the α,β-unsaturated carboxylic acid derivative represented by Formula (5) can be performed pursuant to the process described in the reaction between the compound (A) and the compound (B).

According to the process of the present invention, an α,γ-dihydroxycarboxylic acid derivative (a kind of the compounds represented by Formula (4)) represented by following Formula (7) is formed as a reaction intermediate:

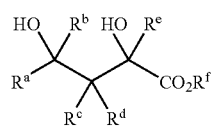

(7)

wherein $R^a$, $R^b$, $R^c$, $R^d$, $R^e$ and $R^f$ have the same meanings as defined above. This compound is supposed to be formed in the following manner. A 1-hydroxyalkyl radical corresponding to the alcohol represented by Formula (2) is formed in the system, attacks and is added to the beta-position of the α,β-unsaturated carboxylic acid derivative represented by Formula (5), and oxygen attacks a radical at the alpha-position formed as a result of the addition to thereby yield the compound in question. The formed α,γ-dihydroxycarboxylic acid derivative represented by Formula (7) undergoes cyclization under reaction conditions and thereby yields the target α-hydroxy-γ-butyrolactone derivative represented by Formula (6).

When a primary alcohol is used as the alcohol represented by Formula (2) (i.e., when $R^a$ is a hydrogen atom), a β-acyl-α-hydroxycarboxylic acid derivative of following Formula (8) may be formed in addition to the compound represented by Formula (6):

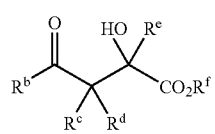

(8)

wherein $R^b$, $R^c$, $R^d$, $R^e$, and $R^f$ have the same meanings as defined above. This is provably because an acyl radical [$R^bC(=O)\cdot$] is formed in the system. The α-hydroxy-γ-butyrolactone derivative can also be prepared by isolating the α,γ-dihydroxycarboxylic acid derivative represented by Formula (7), for example, dissolving the same in a solvent, and heating the solution according necessity, as mentioned above.

3. Production of Conjugated Unsaturated Compounds

By catalysis of the cyclic imide compound, an alcohol represented by following Formula (2a):

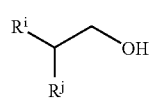

(2a)

wherein $R^i$ and $R^j$ are the same or different and are each a hydrogen atom or an organic group, where $R^i$ and $R^j$ may be combined to form a ring with the adjacent carbon atom, is allowed to react with oxygen and an active olefin represented by following Formula (3a):

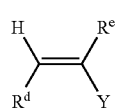

(3a)

wherein $R^d$ and $R^e$ are the same or different and are each a hydrogen atom or an organic group; and Y is an electron attractive group, where at least two of $R^d$, $R^e$ and Y may be combined to form a ring with the adjacent carbon atom or carbon-carbon bond, and thereby yields a conjugated unsaturated compound represented by following Formula (9):

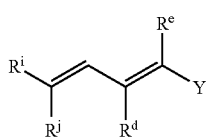

(9)

wherein $R^d$, $R^e$, $R^i$, $R^j$ and Y have the same meanings as defined above. This reaction can be performed pursuant to the process described in PCT International Publication Number WO 00/35835 (the process using N-hydroxyphthalimide or another catalyst).

Organic groups in $R^i$ and $R^j$ in Formula (2a) are groups similar to the organic groups in $R^a$ and $R^b$. The rings formed by $R^i$ and $R^j$ with the adjacent carbon atom include similar rings to those formed by $R^a$ and $R^b$ with the adjacent carbon atom.

Preferred substituent $R^i$ includes, for example, hydrogen atom, $C_1$-$C_4$ alkyl groups and $C_6$-$C_{14}$ aryl groups. Preferred $R^j$ includes, for example, hydrogen atom, $C_1$-$C_{10}$ aliphatic hydrocarbon groups (especially $C_1$-$C_{10}$ alkyl groups) and alicyclic hydrocarbon groups (e.g., $C_3$-$C_{15}$ cycloalkyl groups or cycloalkenyl groups; and bridged cyclic hydrocarbon groups). Alternatively, $R^i$ and $R^j$ are preferably combined to form a non-aromatic carbon ring having from about 3 to about 15 members (particularly from about 5 to about 8 members) with the adjacent carbon atom.

The alcohols represented by Formula (2a) include a wide variety of primary alcohols. Typical examples of such alcohols are ethanol, 1-propanol, 1-butanol, 2-methyl-1-propanol, 1-pentanol, 1-hexanol, and other saturated or unsaturated aliphatic primary alcohols each having from about 2 to about 30 (preferably from about 2 to about 20, and more preferably from about 2 to about 15) carbon atoms; cyclopentylmethyl alcohol, cyclohexylmethyl alcohol, and other saturated or unsaturated alicyclic primary alcohols; 2-phenylethyl alcohol, 3-phenylpropyl alcohol, cinnamic alcohol, and other aromatic primary alcohols; and 2-(2-hydroxyethyl)pyridine, and other heterocyclic alcohols.

The compounds represented by Formula (3a) correspond to compounds represented by Formula (3) where $R^c$ is a hydrogen atom. The substituents $R^d$, $R^e$, and Y in Formula (3a) are similar to those in Formula (3).

A reaction can be performed pursuant to the production of the 1,3-dihydroxy compound. In this reaction, a compound corresponding to Formula (4) (a compound of Formula (4) where $R^a$=$R^iR^jCH$ group and $R^b$=$R^c$=H) can be formed in addition to the conjugated unsaturated compound represented by Formula (9). When a compound represented by Formula (3a), where Y is a $CO_2R^f$ group, is used as the compound of Formula (3a), a compound corresponding to Formula (6) (a compound of Formula (6) where $R^a$=$R^iR^jCH$ group and $R^b$=$R^c$=H) can be formed in addition to the conjugated unsaturated compound represented by Formula (9).

For example, when n-propyl alcohol is allowed to react with ethyl acrylate, ethyl 2,4-dihydroxyhexanoate corresponding to Formula (4) and 4-ethyl-2-hydroxy-γ-butyrolactone corresponding to Formula (6) are formed in addition to the target ethyl sorbate under some conditions.

The conjugated unsaturated compound represented by Formula (9) is supposed to be formed in the following manner. Initially, a dihydroxy compound corresponding to Formula (4) [a compound of Formula (4) where $R^a$=$R^iR^jCH$ group, and $R^b$=$R^c$=H] is formed, two molecules of water are then eliminated from this compound and thereby yields the compound in question. Reaction products can be separated and purified in the same separation means as above.

4. Production of β-Hydroxyacetal Compounds

By catalysis of the cyclic imide compound, an acetal represented by following Formula (10):

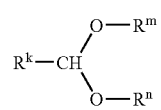

(10)

wherein $R^k$, $R^m$ and $R^n$ are the same or different and are each a hydrogen atom or an organic group, where $R^m$ and $R^n$ may be combined to form a ring with the adjacent two oxygen atoms and the carbon atom indicated in the formula, is allowed to react with oxygen and the active olefin represented by Formula (3) and thereby yields a β-hydroxyacetal compound represented by following Formula (11):

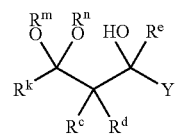

(11)

wherein $R^c$, $R^d$, $R^e$, $R^k$, $R^m$, $R^n$ and Y have the same meanings as defined above. This reaction can be performed pursuant to the process described in PCT International Publication Number WO 00/35835 (the process using N-hydroxyphthalimide or another catalyst).

In Formula (10), organic groups in $R^k$, $R^m$ and $R^n$ include organic groups similar to those in $R^a$ and $R^b$. The rings formed by $R^m$ and $R^n$ with the adjacent two oxygen atoms and the carbon atom include, for example, 1,3-dioxolane ring and 1,3-dioxane ring. With these rings, substituents such as alkyl groups and halogen atoms can be bonded.

Preferred substituent $R^k$ includes, for example, hydrogen atom; $C_1$-$C_{10}$ aliphatic hydrocarbon groups (especially, $C_1$-$C_4$ alkyl groups); alicyclic hydrocarbon groups (cycloalkyl groups, cycloalkenyl groups and bridged cyclic hydrocarbon groups) each having from about 3 to about 15 carbon atoms; and $C_6$-$C_{14}$ aryl groups. Preferred substituents $R^m$ and $R^n$ include, for example, hydrogen atom; $C_1$-$C_6$ aliphatic hydrocarbon groups (particularly, $C_1$-$C_4$ alkyl groups); and alicyclic hydrocarbon groups each having from about 3 to about 10 carbon atoms. Alternatively, $R^m$ and $R^n$ are preferably combined to form a ring with the adjacent two oxygen atoms and carbon atom.

The acetals represented by Formula (10) include compounds exemplified as the acetals each having a carbon-hydrogen bond at the adjacent position to an oxygen atom in the compounds (A1-3). Typical examples of such acetals include 1,3-dioxolane, 2-methyl-1,3-dioxolane, 2-ethyl-1,3-dioxolane, and other 1,3-dioxolane compounds; 2-methyl- 1,3-dioxane, and other 1,3-dioxane compounds; and acetaldehyde dimethyl acetal, and other dialkyl acetals.

The active olefin represented by Formula (3) is the same as stated above. A reaction can be performed according to the process of the present invention for producing an organic compound. Reaction products can be separated and purified in a similar separation means to those mentioned above.

In this reaction, the β-hydroxyacetal compound represented by Formula (11) is supposed to be formed in the following manner. Initially, a 1,1-di-substituted oxyalkyl radial corresponding to the acetal represented by Formula (10) is formed, this radical attacks and is added to a carbon atom at the beta-position of the group Y between the two carbon atoms constituting an unsaturated bond of the active olefin represented by Formula (3), and oxygen attacks a radical at the alpha-position formed as a result of the addition and thereby yields the compound in question.

5. Production of Hydroxy Compounds

By catalysis of the cyclic imide compound, a compound having a methine carbon atom and represented by following Formula (12):

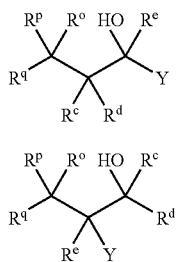
(12)

wherein $R^o$, $R^p$ and $R^q$ are the same or different and are each an organic group, where at least two of $R^o$, $R^p$ and $R^q$ may be combined to form a ring with the adjacent carbon atom, is allowed to react with oxygen and the active olefin represented by Formula (3) and thereby yields at least one of hydroxy compounds represented by following Formulae (13) and (14):

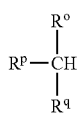
(13)

(14)

wherein $R^c$, $R^d$, $R^e$, $R^o$, $R^p$, $R^q$ and Y have the same meanings as defined above. This reaction can be performed pursuant to the process described in PCT International Publication Number WO 00/35835 (the process using N-hydroxyphthalimide or another catalyst).

The organic groups in $R^o$, $R^p$ and $R^q$ in Formula (12) include organic groups similar to those in $R^a$ and $R^b$. Preferred organic groups are, for example, $C_1$-$C_{10}$ aliphatic hydrocarbon groups (especially, $C_1$-$C_4$ alkyl groups); alicyclic hydrocarbon groups (cycloalkyl groups, cycloalkenyl groups and bridged cyclic hydrocarbon groups) each having from about 3 to about 15 carbon atoms; and $C_6$-$C_{14}$ aryl groups.

The rings formed by at least two of $R^o$, $R^p$ and $R^q$ ($R^o$ and $R^p$, $R^p$ and $R^q$, $R^o$ and $R^q$, or $R^o$ and $R^p$ and $R^q$) with the adjacent carbon atom include, but are not limited to, cyclopentane, cyclohexane, and other monocyclic alicyclic carbon rings (cycloalkane rings and cycloalkene rings) each having from about 3 to about 20 members (preferably from about 3 to about 15 members, more preferably from about 5 to about 15 members, and typically from about 5 to about 8 members); adamantane ring, perhydroindene ring, decalin ring, perhydrofluorene ring, perhydroanthracene ring, perhydrophenanthrene ring, tricyclo[5.2.1.0$^{2,6}$]decane ring, perhydroacenaphthene ring, perhydrophenalene ring, norbornane ring, norbornene ring, and other bridged carbon rings each having from about two to about four rings. These rings may each have at least one substituent.

When $R^o$, $R^p$ and $R^q$ are combined to form a bridged cyclic carbon ring with the adjacent carbon atom, the methine carbon atom indicated in Formula (12) should preferably be a carbon atom at a bridgehead position.

The compounds represented by Formula (12) each having a methine carbon atom include, for example, compounds exemplified as the compounds (A3) each having a methine carbon atom, such as the bridged cyclic compounds (A3-1a), the non-aromatic cyclic compounds (A3-1b) each having a hydrocarbon group combined with a ring, and the chain compounds (A3-2) each having a methine carbon atom.

The active olefins represented by Formula (3) are the same as mentioned above. A reaction can be performed according to the process of the present invention for producing an organic compound. Reaction products can be separated and purified by a similar separation means to those mentioned above.

In this reaction, the hydroxy compound represented by Formula (13) or the hydroxy compound represented by Formula (14) is supposed to be formed in the following manner. A radical is formed at the methine carbon position of the compound represented by Formula (12), then attacks and is added to a carbon atom at the alpha-position or a carbon atom at the beta-position of the group Y between the two carbon atoms constituting an unsaturated bond of the active olefin represented by Formula (3), and oxygen attacks a radical at the alpha-position or beta-position formed as a result of the addition and thereby yields the hydroxy compound in question.

Of the hydroxy compounds represented by Formula (13) thus prepared, preferred are compounds where $R^o$, $R^p$ and $R^q$ are combined to form a bridged cyclic carbon ring (e.g., an adamantane ring) with the adjacent carbon atom, each of $R^c$, $R^d$, and $R^e$ is a hydrogen atom or a $C_1$-$C_4$ alkyl group, Y is an alkoxycarbonyl group (e.g., a $C_1$-$C_4$ alkoxy-carbonyl group), an aryloxycarbonyl group, an acyl group (e.g., a $C_1$-$C_4$ acyl group or a benzoyl group) or a carboxyl group. Such compounds are useful as, for example, materials for pharmaceuticals, agricultural chemicals, and other fine chemicals, and materials for functional polymers.

6. Production of Carbonyl Compounds (1)

By catalysis of the cyclic imide compound, the compound having a methine carbon atom represented by Formula (12) is allowed to react with oxygen and an active olefin represented by following Formula (3b):

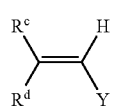
(3b)

wherein $R^c$ and $R^d$ are the same or different and are each a hydrogen atom or an organic group; and Y is an electron attractive group, where at least two of $R^c$, $R^d$ and Y may be combined to form a ring with the adjacent carbon atom or carbon-carbon bond, and thereby yields a carbonyl compound represented by following Formula (15):

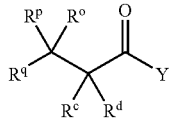

(15)

wherein $R^c$, $R^d$, $R^o$, $R^p$, $R^q$ and Y have the same meanings as defined above. This reaction can be performed pursuant to the process described in PCT International Publication Number WO 00/35835 (the process using N-hydroxyphthalimide or another catalyst).

This process corresponds to the production of the hydroxy compound in which a compound having a hydrogen atom as $R^e$ is employed as the active olefin represented by Formula (3). In this case, the carbonyl compound represented by Formula (15) is formed instead of, or in addition to, a compound corresponding to Formula (13) ($R^e$=H) and/or a compound corresponding to Formula (14) ($R^e$=H). The proportion of the formed two compounds can be controlled by appropriately selecting reaction conditions such as reaction temperature, amount of the catalyst, and the type of the promoter (metallic compound). The carbonyl compound represented by Formula (15) is supposed to be formed by the oxidation of the compound corresponding to Formula (13) ($R^e$=H) in a system.

Of the carbonyl compounds represented by Formula (15) thus prepared, preferred are compounds where $R^o$, $R_p$, and $R^q$ are combined to form a bridged cyclic carbon ring (e.g., an adamantane ring) with the adjacent carbon atom, each of $R^c$ and $R^d$ is a hydrogen atom or a $C_1$-$C_4$ alkyl group, Y is an alkoxycarbonyl group (e.g., a $C_1$-$C_4$ alkoxy-carbonyl group), an aryloxycarbonyl group, an acyl group (e.g., a $C_1$-$C_4$ acyl group or a benzoyl group) or a carboxyl group. Such compounds are useful as, for example, materials for pharmaceuticals, agricultural chemicals and other fine chemicals, and materials for functional polymers.

7. Production of Compounds having Electron Attractive Group

By catalysis of the cyclic imide compound, the compound represented by Formula (12) having a methine carbon atom is allowed to react with oxygen and an active olefin represented by following Formula (3c):

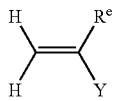

(3c)

wherein $R^e$ is a hydrogen atom or an organic group; and Y is an electron attractive group, and thereby yields a compound having an electron attractive group and represented by following Formula (16):

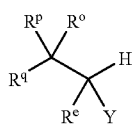

(16)

wherein $R^e$, $R^o$, $R^p$, $R^q$ and Y have the same meanings as defined above. This reaction can be performed pursuant to the process described in PCT International Publication Number WO 00/35835 (the process using N-hydroxyphthalimide or another catalyst).

This process corresponds to the production of the hydroxy compound in which a compound having hydrogen atoms as $R^c$ and $R^d$ is employed as the active olefin represented by Formula (3). In this process, the compound represented by Formula (16) is formed instead of, or in addition to, a compound corresponding to Formula (13) ($R^c$=$R^d$=H), a compound corresponding to Formula (14) ($R^c$=$R^d$=H) or a compound corresponding to Formula (15) (only in the case where $R^c$=$R^d$=H, and $R^e$=H). The proportions of the individual product compounds can be controlled by appropriately selecting reaction conditions such as reaction temperature, amount of the catalyst, and the type of the promoter (metallic compound).

The compound represented by Formula (16) is supposed to be formed in the following manner. The methylol group of a compound corresponding to Formula (14) ($R^c$=$R^d$=H) is further oxidized in the system to yield a carboxyl group, and the carboxyl group undergoes decarboxylation to thereby yield the compound in question.

Of the compounds represented by Formula (16) thus prepared, preferred are compounds where $R^o$, $R^p$, and $R^q$ are combined to form a bridged cyclic carbon ring (e.g., an adamantane ring) with the adjacent carbon atom, $R^e$ is a hydrogen atom or a $C_1$-$C_4$ alkyl group, and Y is an alkoxycarbonyl group (e.g., a $C_1$-$C_4$ alkoxy-carbonyl group), an aryloxycarbonyl group, an acyl group (e.g., a $C_1$-$C_4$ acyl group or a benzoyl group) or a carboxyl group. Such compounds are useful as, for example, materials for pharmaceuticals, agricultural chemicals and other fine chemicals, and materials for functional polymers.

8. Production of Alcohols

By catalysis of the cyclic imide compound and where necessary in the presence of oxygen, the alcohol represented by Formula (2) is allowed to react with the compound represented by Formula (12) having a methine carbon atom and thereby yields an alcohol represented by following Formula (17):

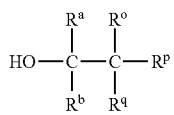

(17)

wherein $R^a$, $R^b$ $R^o$, $R^p$, $R^q$ and Y have the same meanings as defined above. This reaction can be performed pursuant to the process described in PCT International Publication Number WO 00/35835 (the process using N-hydroxyphthalimide or another catalyst).

The alcohols represented by Formula (2) include similar alcohols as in the production of the 1,3-dihydroxy compounds. The compounds represented by Formula (12) having a methine carbon atom include similar compounds as in the production of the hydroxy compounds. In this process, the compound represented by Formula (12) having a methine carbon atom is supposed to serve as the radical scavenging compound (B2).

A reaction can be performed in accordance with the process of the present invention for producing an organic compound. Reaction products can be separated and purified by a similar separation means to those mentioned above.

In this reaction, the alcohol represented by Formula (17) is supposed to be formed in the following manner. A 1-hydroxyalkyl radical corresponding to the alcohol represented by Formula (2) is formed in a system, then attacks the methine carbon atom of the compound represented by Formula (12) and thereby yields the alcohol in question.

9. Production of Coupling Products

By catalysis of the cyclic imide compound and where necessary in the presence of oxygen, a compound having a methine carbon atom and represented by following Formula (12a):

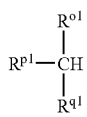

(12a)

wherein $R^{o1}$, $R^{p1}$ and $R^{q1}$ are the same or different and are each an organic group, where at least two of $R^{o1}$, $R^{p1}$ and $R^{q1}$ may be combined to form a ring with the adjacent carbon atom, is allowed to react with a compound having a methine carbon atom and represented by following Formula (12b):

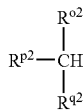

(12b)

wherein $R^{o2}$, $R^{p2}$ and $R^{q2}$ are the same or different and are each an organic group, where at least two of $R^{o2}$, $R^{p2}$ and $R^{q2}$ may be combined to form a ring with the adjacent carbon atom, and thereby yields a coupling product (a hydrocarbon) represented by following Formula (18):

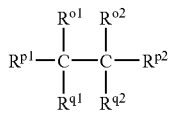

(18)

wherein $R^{o1}$, $R^{p1}$, $R^{q1}$, $R^{o2}$, $R^{p2}$ and $R^{q2}$ have the same meanings as defined above. This reaction can be performed pursuant to the process described in PCT International Publication Number WO 00/35835 (the process using N-hydroxyphthalimide or another catalyst).

In Formulae (12a) and (12b), the organic groups and preferred organic groups in $R^{o1}$, $R^{p1}$, $R^{q1}$, $R^{o2}$, $R^{p2}$ and $R^{q2}$ include groups similar to those in $R^o$, $R^p$ and $R^q$. The rings formed by at least two of $R^{o1}$, $R^{p1}$ and $R^{q1}$ ($R^{o1}$ and $R^{p1}$, $R^{p1}$ and $R^{q1}$, $R^{q1}$ and $R^{o1}$, or $R^{o1}$ and $R^{p1}$ and $R^{q1}$) with the adjacent carbon atom, and the rings formed by at least two of $R^{o2}$, $R^{p2}$ and $R^{q2}$ ($R^{o2}$ and $R^{p2}$, $R^{p2}$ and $R^{q2}$, $R^{o2}$ and $R^{q2}$, or $R^{o2}$ and $R^{p2}$ and $R^{q2}$) with the adjacent carbon atom include rings similar to those formed by at least two of $R^o$, $R^p$ and $R^q$ with the adjacent carbon atom.

The compounds represented by Formulae (12a) and (12b) each having a methine carbon atom include the compounds exemplified as the compounds (A3), such as the bridged cyclic compounds (A3-1a), the non-aromatic cyclic compounds (A3-1b) each having a hydrocarbon group combined with a ring, and the chain compounds (A3-2) each having a methine carbon atom. The compound represented by Formula (12a) and the compound represented by Formula (12b) may be identical to, or different from, each other.

A reaction can be performed in accordance with the process of the present invention for producing an organic compound. Reaction products can be separated and purified by a similar separation means to those mentioned above.

In this reaction, the coupling product represented by Formula (18) is supposed to be formed in the following manner. A radical is formed at the methine carbon position of the compound represented by Formula (12a), attacks the methine carbon atom of the compound represented by Formula (12b) and thereby yields the coupling product in question.

10. Production of Carbonyl Compounds (2)

By catalysis of the cyclic imide compound and where necessary in the presence of oxygen, an aldehyde represented by following Formula (19):

$R^g$CHO (19)

wherein $R^g$ is a hydrogen atom or an organic group, is allowed to react with an olefin represented by following Formula (20):

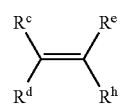

(20)

wherein $R^c$, $R^d$, $R^e$ and $R^h$ are the same or different and are each a hydrogen atom or an organic group, where at least two of $R^c$, $R^d$, $R^e$ and $R^h$ may be combined to form a ring with the adjacent carbon atom or carbon-carbon bond, and thereby yields a carbonyl compound represented by following Formula (21):

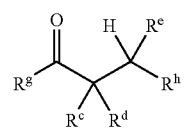

(21)

wherein $R^c$, $R^d$, $R^e$, $R^h$ and $R^g$ have the same meanings as defined above.

In Formula (19), the organic groups in $R^g$ include similar organic groups to those in $R^a$ and $R^b$. As the aldehyde represented by Formula (19), the aldehydes exemplified in the carbonyl-group-containing compounds (A2-1) can be used.

In Formula (20), $R^c$, $R^d$ and $R^e$ have the same meanings as defined above, and the organic groups in $R^h$ include similar organic groups to those in $R^c$, $R^d$ and $R^e$. As the olefin represented by Formula (20), the compounds exemplified as the inert olefins (B1-6) and active unsaturated compounds (B1-1) can be used.

A reaction can be performed in accordance with the process of the present invention for producing an organic compound. Reaction products can be separated and purified by a similar separation means to those mentioned above.

In this reaction, the carbonyl compound represented by Formula (21) is supposed to be formed in the following manner. A corresponding acyl radical is formed from the compound represented by Formula (19), then attacks the carbon atom constituting the double bond of the compound represented by Formula (20) and thereby yields the carbonyl compound in question.

11. Production of β-Acyloxycarboxylic Acids or β-Acyloxyketones

By catalysis of the cyclic imide compound and in the presence of oxygen, the alcohol represented by Formula (2) is allowed to react with an α,β-unsaturated carbonyl compound represented by following Formula (22):

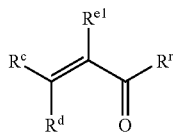

(22)

wherein $R^c$ and $R^d$ are the same or different and are each a hydrogen atom or an organic group; and $R^{e1}$ and $R^r$ are the same or different and are each a hydrogen atom, a hydrocarbon group or a heterocyclic group, where $R^c$ and $R^d$ may be combined to form a ring with the adjacent carbon atom, and thereby yields a β-acyloxycarboxylic acid or β-acyloxyketone represented by following Formula (23):

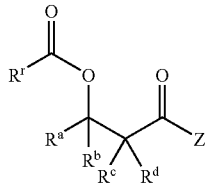

(23)

wherein Z is a hydroxyl group when $R^{e1}$ in Formula (22) is a hydrogen atom, and Z is the substituent $R^{e1}$ when $R^{e1}$ is a hydrocarbon group or a heterocyclic group; and $R^a$, $R^b$, $R^c$, $R^d$ and $R^r$ have the same meanings as defined above. This reaction can be performed pursuant to a process described in Japanese Patent Application No. 2000-648 (a process using N-hydroxyphthalimide or another catalyst).

The organic groups, hydrocarbon groups, heterocyclic groups, and the rings formed by $R^c$ and $R^d$ with the adjacent carbon atom include similar groups as mentioned above.

According to this reaction, for example, 2-propanol is allowed to react with methyl vinyl ketone and thereby yields 3-acetoxy-3-methylbutanoic acid. Likewise, 2-propanol is allowed to react with acrolein and thereby yields 3-formyloxy-3-methylbutanoic acid.

The reaction can be performed pursuant to the process of the present invention for producing an organic compound. Reaction products can be separated and purified by a similar separation means to those mentioned above.

In this reaction, the target β-acyloxycarboxylic acid or β-acyloxyketone represented by Formula (23) is supposed to be formed in the following manner. A 1-hydroxyalkyl radical corresponding to the alcohol represented by Formula (2) is formed in the reaction system, then attacks and is added to the beta-position of the α,β-unsaturated carbonyl compound represented by Formula (22), oxygen attacks a radical formed at the alpha-position as a result of the addition and thereby yields an α,γ-dihydroxycarbonyl compound represented by following Formula (24):

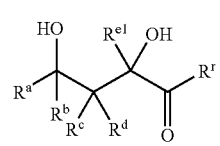

(24)

wherein $R^a$, $R^b$, $R^c$, $R^d$, $R^{e1}$ and $R^r$ have the same meanings as defined above. This compound further undergoes rearrangement of an acyl group ($R^rC=O$ group) and oxidation of a carbon atom, to which the acyl group has been bonded, and thereby yields the target β-acyloxycarboxylic acid or β-acyloxyketone represented by Formula (23). When an α,β-unsaturated carbonyl compound represented by Formula (22), where $R^{e1}$ is a hydrogen atom, is used as the starting compound, a corresponding β-acyloxycarboxylic acid is formed. When an α,β-unsaturated carbonyl compound represented by Formula (22), where $R^{e1}$ is a hydrocarbon group or heterocyclic group, is used as the starting compound, a corresponding β-acyloxyketone is formed.

12. Production of Polyacrylamide Polymers

In the presence of the imide compound and the compound (A) capable of forming a radial, an α,β-unsaturated carboxamide is polymerized under mild conditions and thereby yields a corresponding polyacrylamide polymer [Japanese Patent Application No. 2000-345822 (a process using N-hydroxyphthalimide or another catalyst)].

Typical examples of the α,β-unsaturated carboxamide are (meth)acrylamide, N-methyl(meth)acrylamide, N,N-dimethyl(meth)acrylamide, N-isopropyl(meth)acrylamide, N-phenyl(meth)acrylamide and crotonamide.

A reaction temperature can appropriately be set depending on the type of the raw material and other factors and is, for example, from about 0° C. to about 150° C. and preferably from about 10° C. to about 100° C. The molecular weight of the resulting polymer can be controlled by controlling the reaction temperature. The reaction product can be separated and purified by, for example, precipitation or reprecipitation.

13. Production of Organic Compounds having Oxygen-atom-containing Group

By catalysis of the cyclic imide compound, the compound (A) capable of forming a radical is allowed to react with the oxygen-atom-containing reacting agent (B4) and thereby yields an organic compound having an oxygen-atom-containing group.

This reaction is performed in the presence of, or in the absence of, a solvent. Such solvents include the aforementioned solvents. The amount of the cyclic imide compound catalyst is, for example, from about 0.000001 to about 1 mole, preferably from about 0.00001 to about 0.5 mole, more preferably from about 0.0001 to about 0.4 mole, and often from about 0.001 to about 0.3 mole, relative to 1 mole of the compound (A). This reaction may significantly be accelerated in many cases when a promoter such as the metallic compound (e.g., a vanadium compound, molybdenum compound, manganese compound or cobalt compound) is used in combination with the cyclic imide compound.

When the oxygen-atom-containing reacting agent (B4) is gaseous, it may be diluted with an inert gas such as nitrogen gas or argon gas. Each of the oxygen-atom-containing reacting agents (B4) can be used alone or in combination. By using two or more types of the oxygen-atom-containing reacting agents (B4) in combination, two or more types of different functional groups can be introduced into the molecule. Such functional groups include, for example, hydroxyl group, oxo group, carboxyl group, nitro group and sulfonic acid group. In the combination use, two types or more of thee oxygen-atom-containing reacting agents (B4) can be used concurrently or sequentially.

The amount of the oxygen-atom-containing reacting agent (B4) depends on the type thereof and can appropriately be set in view of reactivity and operability. For example, when oxygen (B4-1) is used as the oxygen-atom-containing reacting agent (B4), the amount of oxygen is equal to or more than about 0.5 mole (e.g., equal to or more than about 1 mole), preferably from about 1 to about 100 moles, and more preferably from about 2 to about 50 moles, relative to 1 mole of the compound (A) Oxygen is often used in a molar excess to the compound (A).

When carbon monoxide (B4-2) and oxygen (B4-1) are used in combination as the oxygen-atom-containing reacting agents (B4), equal to or more than about 1 mole (e.g., from about 1 to about 100 moles) of carbon monoxide and equal to or more than about 0.5 mole (e.g., from about 0.5 to about 50 moles) of oxygen are often used relative to 1 mole of the compound (A). In the combination use, the molar ratio of carbon monoxide to oxygen is from about 1/99 to about 99.99/0.01, and preferably from about 10/90 to about 99/1.

When the nitrogen oxide (B4-3) is used as the oxygen-atom-containing reacting agent (B4), the amount of the nitrogen oxide can appropriately be set depending on the types of the nitrogen oxide and the compound (A) and may be equal to or more than 1 mole or may be less than 1 mole, relative to 1 mole of the compound (A). By using the nitrogen oxide (e.g., nitrogen dioxide) in an amount of less than 1 mole (e.g., equal to or more than about 0.0001 mole and less than 1 mole), preferably from about 0.001 to about 0.8 mole and more preferably from about 0.005 to about 0.25 mole relative to 1 mole of the compound (A), the conversion from the nitrogen oxide and the selectivity of the reaction can significantly be improved.

By using nitrogen dioxide ($NO_2$) in combination with oxygen, the rate of a reaction such as nitration reaction can significantly be improved. In the combination use, the amount of oxygen is equal to or more than about 0.5 mole (e.g., equal to or more than about 1 mole), preferably from about 1 to about 100 moles, and more preferably from about 2 to about 50 moles, relative to 1 mole of nitrogen dioxide.

When the sulfur oxide (B4-4) is used as the oxygen-atom-containing reacting agent (B4), the amount of the sulfur oxide can appropriately be set depending on the types of the sulfur oxide and the compound (A) and is generally from about 1 to about 50 moles, and preferably from about 1.5 to about 30 moles, relative to 1 mole of the compound (A). The reaction can be performed in large excess of the sulfur oxide. When the sulfur oxide (e.g., sulfur dioxide) is used in combination with oxygen, the molar ratio of the sulfur oxide to the oxygen is, for example, from about 10/90 to about 90/10 and more preferably from about 30/70 to about 70/30.

A reaction temperature can appropriately be set depending on, for example, the types of the compound (A) and the oxygen-atom-containing reacting agent (B4). For example, when oxygen (B4-1) is used as the oxygen-atom-containing reacting agent (B4), the reaction temperature is from about 0° C. to about 300° C. and preferably from about 20° C. to about 250° C.

When carbon monoxide (B4-2) and oxygen (B4-1) are used as the oxygen-atom-containing reacting agents (B4), the reaction temperature is, for example, from about 0° C. to about 200° C. and preferably from about 10° C. to about 150° C. When the nitrogen oxide (B4-3) or sulfur oxide (B4-4) is used as the oxygen-atom-containing reacting agent (B4) (including the case where oxygen is used in combination), the reaction temperature is, for example, from about 0° C. to about 150° C. and preferably from about 10° C. to about 125° C. The reaction can be performed at atmospheric pressure or under a pressure (under a load). When the reaction is performed under a pressure, the pressure is generally from about 0.1 to about 10 MPa, and preferably from about 0.2 to about 7 MPa. The reaction can be performed in a conventional system such as a batch system, semi-batch system or continuous system.

After the completion of the reaction, reaction products can be separated and purified by a technique such as filtration, concentration, distillation, extraction, crystallization, recrystallization, adsorption or column chromatography, or any combination of these separation means.

This process can yield a reaction product corresponding to the oxygen-atom-containing reacting agent in a high yield under mild conditions.

Specifically, when oxygen (B4-1) is used as the oxygen-atom-containing reacting agent (B4), an oxidation reaction proceeds and thereby yields a corresponding oxidation product [Japanese Unexamined Patent Application Publications No. 8-38909, No. 9-327626, No. 10-286467 and No. 2000-219650 (reactions using N-hydroxyphthalimide or another catalyst)]. For example, when the heteroatom-containing compound (A1) having a carbon-hydrogen bond at the adjacent position to the heteroatom is used as the compound (A), a carbon atom at the adjacent position to the heteroatom is oxidized. For example, a primary alcohol yields a corresponding aldehyde or carboxylic acid, and a secondary alcohol yields a corresponding ketone. A 1,3-diol yields a corresponding hydroxyketone, and a 1,2-diol yields a corresponding carboxylic acid as a result of oxidative cleavage [Japanese Unexamined Patent Application Publications No. 2000-212116 and No. 2000-219652 (reactions using N-hydroxyphthalimide or another catalyst)]. An ether yields a corresponding ester or acid anhydride [Japanese Unexamined Patent Application Publication No. 10-316610 (a reaction using N-hydroxyphthalimide or another catalyst)]. In addition, a primary or secondary alcohol yields hydrogen peroxide [PCT International Publication Number WO 00/46145 (a reaction using N-hydroxyphthalimide or another catalyst)].

When the compound (A2) having a carbon-heteroatom double bond is used as the compound (A), an oxidation product depending on the type of the heteroatom and other factors can be obtained. For example, by oxidizing a ketone, a carboxylic acid or another product is produced as a result of cleavage. A cyclic ketone such as cyclohexanone yields a dicarboxylic acid such as adipic acid. By using the heteroatom-containing compound (A1) having a carbon-hydrogen bond at the adjacent position to the heteroatom such as a secondary alcohol (e.g., benzhydrol) as a co-reacting agent (co-oxidizing agent), a Baeyer-Villiger type reaction proceeds under mild conditions. As a result, a cyclic ketone yields a corresponding lactone, and a chain ketone yields a corresponding ester in high yields [PCT International Publication Number WO 99/50204 (reactions using N-hydroxyphthalimide or another catalyst)]. In addition, an aldehyde yields a corresponding carboxylic acid.

The compound (A3) having a methine carbon atom as the compound (A) can yield an alcohol derivative having a hydroxyl group introduced into the methine carbon in a high yield. For example, by oxidizing a bridged cyclic hydrocarbon (A3-1a) such as adamantane, alcohol derivatives each having a hydroxyl group at a bridgehead position, such as 1-adamantanol, 1,3-adamantanediol and 1,3,5-adamantanetriol, can be produced with high selectivity. The chain compound (A3-2) having a methine carbon atom, such as isobutane, can yield a tertiary alcohol such as t-butanol in a high yield [Japanese Unexamined Patent Application Publication No. 10-310543 (a reaction using N-hydroxyphthalimide or another catalyst)].

By using the compound (A4) having a carbon-hydrogen bond at the adjacent position to an unsaturated bond as the compound (A), the adjacent position to the unsaturated bond is efficiently oxidized and thereby yields, for example, an alcohol, carboxylic acid or ketone. For example, a compound having a methyl group at the adjacent position to an unsaturated bond yields a primary alcohol or carboxylic acid in a high yield [Japanese Unexamined Patent Application Publications No. 8-38909, No. 9-327626 and No. 11-106377 (reactions using N-hydroxyphthalimide or another catalyst)]. Likewise, a compound having a methylene group or methine group at the adjacent position to an unsaturated bond yields a secondary or tertiary alcohol, ketone or carboxylic acid in a high yield, depending on reaction conditions.

More specifically, an aromatic compound having an alkyl group or a lower-order oxidized group thereof combined with an aromatic ring yields an aromatic carboxylic acid having a carboxyl group combined with the aromatic ring as a result of oxidation of the alkyl group or the lower-order oxidized group thereof. Such lower-order oxidized groups include, for example, hydroxyalkyl groups, formyl group, formylalkyl groups, and alkyl groups each having an oxo group. For example, benzoic acid is obtained from toluene, ethylbenzene, isopropylbenzene, benzaldehyde or mixtures of these compounds; terephthalic acid is obtained from p-xylene, p-isopropyltoluene, p-diisopropylbenzene, p-tolualdehyde, p-toluic acid, p-carboxybenzaldehyde or mixtures of these compounds; trimellitic acid is obtained from pseudocumene, dimethylbenzaldehyde, dimethylbenzoic acid or mixtures of these compounds; pyromellitic acid is obtained from durene, trimethylbenzaldehyde, trimethylbenzoic acid or mixtures of these compounds; 3-quinolinecarboxylic acid is obtained from, for example, 3-methylquinoline, respectively in high yields. In addition, nicotinic acid is obtained from β-picoline.

For example, a compound having a methylene group at the adjacent position to a carbon-carbon double bond yields a secondary alcohol or ketone. In this case, by using a cobalt(II) salt of an acid having a pKa of less than or equal to 8.0, such as cobalt(II) acetate or cobalt(II) nitrate, is used as the promoter, a corresponding conjugated unsaturated carbonyl compound having an oxo group introduced into the carbon atom of the methylene group can be obtained in a high yield. More specifically, valencene yields nootkatone in a high yield.

By using the non-aromatic cyclic hydrocarbon (A5) as the compound (A), an alcohol, hydroperoxide or ketone having a hydroxyl group or oxo group introduced into a carbon atom constituting a ring is obtained. Under some reaction conditions, the ring is oxidatively cleaved and yields a corresponding dicarboxylic acid. For example, cyclohexane can yield cyclohexyl alcohol, cyclohexanone or adipic acid with high selectivity under appropriately selected conditions. Likewise, a cycloalkane such as cyclohexane yields a bis(1-hydroxycycloalkyl) peroxide such as bis(1-hydroxycyclohexyl) peroxide [Japanese Patent Application No. 2000-345824 (a reaction using N-hydroxyphthalimide or another catalyst)]. By using a strong acid as the promoter, adamantane yields adamantanone in a high yield [Japanese Unexamined Patent Application Publication No. 10-309469 (a reaction using N-hydroxyphthalimide or another catalyst)].

When the conjugated compound (A6) is used as the compound (A), a variety of compounds is formed depending on the structure of the conjugated compound. For example, a conjugated diene yields an alkenediol or other products as a result of oxidation. Specifically, butadiene yields, for example, 2-butene-1,4-diol and/or 1-butene-3,4-diol as a result of oxidation. When an α,β-unsaturated nitrile or α,β-unsaturated carboxylic acid or a derivative thereof is oxidized, the α, β-unsaturated bonding position is selectively oxidized and is converted into a single bond, and the beta-position is converted into a formyl group, an acetal group (in a reaction in the presence of an alcohol) or an acyloxy group (in a reaction in the presence of a carboxylic acid) in the resulting compound. More specifically, by oxidizing acrylonitrile and methyl acrylate in the presence of methanol, 3,3-dimethoxypropionitrile and methyl 3,3-dimethoxypropionate are formed, respectively.

When the amine (A7) is used as the compound (A), a corresponding Schiff base or oxime is formed. When the aromatic compound (A8) is used as the compound (A) in the co-existence of, for example, the compound (A4) having a carbon-hydrogen bond at the adjacent position to an unsaturated bond (e.g., fluorene) as the co-reacting agent (co-oxidizing agent), a corresponding quinone is formed in a good yield [Japanese Unexamined Patent Application Publications No. 11-226416 and No. 11-228484 (reactions using N-hydroxyphthalimide or another catalyst)]. The straight-chain alkane (A9) yields, for example, an alcohol or ketone.

By using the olefin (A10) as the compound (A), a corresponding epoxy compound can be obtained [Japanese Unexamined Patent Application Publication No. 11-49764 and PCT International Publication Number WO 99/50204 (reactions using N-hydroxyphthalimide or another catalyst)]. Specifically, when the heteroatom-containing compound (A1) having a carbon-hydrogen bond at the adjacent position to the heteroatom, such as a secondary alcohol, or the compound (A4) having a carbon-hydrogen bond at the adjacent position to an unsaturated bond is used as the co-reacting agent (co-oxidizing agent), an epoxidation reaction proceeds under mild conditions and thereby yields the corresponding epoxide in a good yield.

By allowing at least one compound selected from cycloalkanes, cycloalkanols and cycloalkanones to react with ammonia and oxygen (B4-1) as the oxygen-atom-containing reacting agent (B4) in the presence of the cyclic imide compound catalyst, a corresponding lactam is obtained [Japanese Patent Application No. 2000-345823 (a reaction using N-hydroxyphthalimide or another catalyst)]. More specifically, by allowing at least one compound selected from cyclohexane, cyclohexanol and cyclohexanone to react with ammonia and oxygen in the presence of the catalyst, ε-caprolactam is obtained.

When carbon monoxide (B4-2) and oxygen (B4-1) are used as the oxygen-atom-containing reacting agents (B4), a carboxylation reaction smoothly proceeds and thereby yields a corresponding carboxylic acid in a good yield

[Japanese Unexamined Patent Application Publication No. 11-239730 (a reaction using N-hydroxyphthalimide or another catalyst)]. For example, when the compound (A3) having a methine carbon atom is used as the compound (A), a carboxyl group is introduced into the methine carbon atom. Likewise, in the compound (A4) having a carbon-hydrogen bond at the adjacent position to an unsaturated bond, a carboxyl group is introduced into a carbon atom relating to the carbon-hydrogen bond. The non-aromatic cyclic hydrocarbon (A5), such as cyclohexane, yields a carboxylic acid having a carboxyl group combined with a carbon atom constituting a ring.

When the nitrogen oxide (B4-3) is used as the oxygen-atom-containing reacting agent (B4), a nitration reaction predominantly proceeds and thereby yields, for example, a corresponding nitro compound [Japanese Unexamined Patent Application Publication No. 11-239730 (a reaction using N-hydroxyphthalimide or another catalyst)]. For example, when the compound (A3) having a methine carbon atom is used as the compound (A), the methine carbon atom is nitrated. Likewise, when the compound (A4) having a carbon-hydrogen bond at the adjacent position to an unsaturated bond is used, a carbon atom relating to the carbon-hydrogen bond is nitrated. The non-aromatic cyclic hydrocarbon (A5), such as cyclohexane, yields a corresponding cyclic nitro compound having a nitro group combined with a carbon atom constituting a ring. Even the straight-chain alkane (A9), such as hexane, can yield a corresponding nitroalkane. When nitrogen dioxide is used as the oxygen-atom-containing reacting agent (B4), the nitration reaction can efficiently proceed by using the substrate in excess to nitrogen dioxide [Japanese Unexamined Patent Application Publication No. 11-136339 (a reaction using N-hydroxyphthalimide or another catalyst)].

When a compound having a methyl group at the adjacent position to an aromatic ring (at a "benzylic position"), such as toluene, is used as the compound (A), a nitro group is introduced into the carbon atom of the methyl group. Under some conditions, the methyl group is converted into a formyl group and thereby yields a corresponding aromatic aldehyde (e.g., benzaldehyde), or a nitro group is introduced into the aromatic ring in the resulting compound. The use of a compound having a methylene group at the adjacent position to an aromatic ring (e.g., ethylbenzene) as the substrate yields a nitro compound (e.g., α-nitroethylbenzene), in which the methylene group is nitrated, and under some reaction conditions, yields an oxime compound (e.g., acetophenone oxime) in which the methylene group is converted into an oxime.

By using nitrogen monoxide as the oxygen-atom-containing reacting agent (B4), an ether yields a corresponding aldehyde as a result of cleavage of the ether bond [Japanese Unexamined Patent Application Publications No. 11-315036 and No. 11-254977 (reactions using N-hydroxyphthalimide or another catalyst)]. For example, phthalan yields phthalaldehyde in a high yield. Likewise, by using nitrogen monoxide as the oxygen-atom-containing reacting agent (B4), a cycloalkane yields a corresponding cycloalkanone oxime [Japanese Patent Application No. 2000-157356 (a reaction using N-hydroxyphthalimide or another catalyst)]. For example, cyclohexane yields cyclohexanone oxime.

By allowing a chain or cyclic compound having a methylene group to react with the nitrogen oxide such as nitrogen monoxide in the presence of the cyclic imide compound catalyst and a halogen (e.g., chlorine) or a Beckmann rearrangement catalyst, a corresponding amide or lactam is obtained [Japanese Patent Application No. 11-372177 (a reaction using N-hydroxyphthalimide or another catalyst)]. For example, cyclohexane yields α-caprolactam.

When the nitric acids are used as the oxygen-atom-containing reacting agent (B4), a nitration reaction predominantly proceeds and thereby yields, for example, a corresponding nitro compound, as in the use of the nitrogen oxide (B4-3) [Japanese Patent Application No. 2000-58054 (a reaction using N-hydroxyphthalimide or another catalyst)]. For example, when the compound (A4) having a carbon-hydrogen bond at the adjacent position to an unsaturated bond is used as the substrate, a carbon atom relating to the carbon-hydrogen bond is nitrated. When the compound (A3) having a methine carbon atom is used as the substrate, the methine carbon atom is nitrated. When the non-aromatic cyclic hydrocarbon (A5) is used as the substrate, a nitro group is introduced into a carbon atom constituting a ring. In this case, a cycloalkane, such as cyclohexane, yields a corresponding nitrocycloalkane. In the non-aromatic heterocyclic compound having a carbon-hydrogen bond at the adjacent position to the heteroatom, a carbon atom relating to the carbon-hydrogen bond is nitrated. Likewise, the straight-chain alkane (A9), such as hexane, yields a corresponding nitroalkane.

This reaction is supposed to proceed in the following manner. The cyclic imide compound reacts with the nitric acids and thereby yields an imido-N-oxy radical, the radical withdraws a hydrogen atom from the substrate and thereby yields another radical, and to the resulting radical, nitrogen dioxide formed in the reaction system is added and thereby yields a corresponding nitro compound.

When the sulfur oxide (B4-4) is used as the oxygen-atom-containing reacting agent (B4), a sulfonation and/or sulfination reaction proceeds and thereby yields a corresponding organic sulfur acid or a salt thereof. For example, when the compound (A3) having a methine carbon atom is used as the compound (A), a sulfur acid group is introduced into the methine carbon atom. When the compound (A4) having a carbon-hydrogen bond at the adjacent position to an unsaturated bond is used, a sulfur acid group (e.g., a sulfonic acid group or sulfinic acid group) is introduced into a carbon atom relating to the carbon-hydrogen bond. The non-aromatic cyclic hydrocarbon (A5), such as cyclohexane, yields an organic sulfur acid having a sulfur acid group combined with a carbon atom constituting a ring. The formed organic sulfur acid can be converted into a corresponding salt thereof according to conventional techniques. For example, the salt can be obtained by reacting the organic sulfur acid with an alkali metal hydroxide, alkali metal carbonate, alkali metal hydrogencarbonate, alkaline earth metal hydroxide, alkaline earth metal carbonate, amine, thiourea or isothiourea in an appropriate solvent such as water.

EXAMPLES

The present invention will be illustrated in further detail with reference to several examples and comparative examples below, which are not intended to limit the scope of the invention. Reaction products were analyzed and identified by gas chromatography, high performance liquid chromatography or other techniques.

Preparation Example 1

In a 3-L flask equipped with a stirrer, a thermometer and a dropping funnel, 110 g (522.39 mmol) of anhydrous trimellitic chloride (4-chlorocarbonylphthalic anhydride) and 770 g of 1,4-dioxane were placed and were stirred at room temperature in an atmosphere of a nitrogen gas. To the resulting mixture, a mixture of 92.70 g (497.52 mmol) of 1-dodecanol, 41.32 g (522.39 mmol) of pyridine and 370 g of 1,4-dioxane was added dropwise over 1 hour. The mixture was stirred at room temperature for further 5 hours, followed by dropwise addition of 570 g of pure water over 30 minutes. Pyridine hydrochloride separated in a reaction system was then dissolved, and a crystal of target 4-dodecyloxycarbonylphthalic anhydride separated out. The resulting mixture was stirred for further 1 hour, the precipitate was separated by filtration and was rinsed with pure water, was then dried at 50° C. under reduced pressure and thereby yielded 145.26 g (402.99 mmol) of 4-dodecyloxycarbonylphthalic anhydride as a white powder. The yield was 80.1% on the basis of 1-dodecanol and 77.1% on the basis of anhydrous trimellitic chloride.

[Spectral Data of 4-Dodecyloxycarbonylphthalic Anhydride]

$^1$H-NMR (CDCl$_3$) δ: 0.88 (t, 3H), 1.20-1.50 (m, 18H), 1.82 (m, 2H), 4.41 (t, 2H), 8.11 (dd, 1H), 8.58 (dd, 2H), 8.64 (dd, 2H)

In a 500-ml flask equipped with a stirrer, a thermometer and a dropping funnel, 100 g (277.43 mmol) of 4-dodecyloxycarbonylphthalic anhydride, 21.21 g (305.17 mmol) of hydroxylamine hydrochloride and 250 g of pyridine were placed and were stirred at room temperature in an atmosphere of nitrogen gas for 30 minutes, followed by stirring at 90° C. for further 3 hours. The resulting reaction mixture was added dropwise to 3000 g of pure water over 30 minutes with stirring and thereby yielded a crystal of 4-dodecyloxycarbonyl-N-hydroxyphthalimide. The mixture was stirred for further 1 hour, the precipitate was separated by filtration and was rinsed with pure water. The resulting solid was stirred and rinsed in a solvent mixture of 640 g of n-hexane and 160 g of ethyl acetate for 3 hours, the resulting slurry was filtrated, was rinsed with n-hexane, was dried at 60° C. under reduced pressure and thereby yielded 90.88 g (242.04 mmol) of target 4-dodecyloxycarbonyl-N-hydroxyphthalimide as a white powder. The yield was 87.2% on the basis of 4-dodecyloxycarbonylphthalic anhydride.

[Spectral Data of 4-Dodecyloxycarbonyl-N-hydroxyphthalimide]

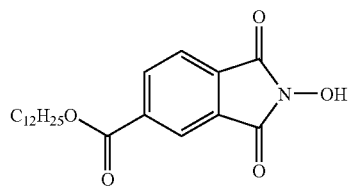

$^1$H-NMR (DMSO-d$_6$) δ: 0.82 (t, 3H), 1.25-1.45 (m, 18H), 1.72 (m, 2H), 4.30 (t, 2H), 7.93 (dd, 1H), 8.15 (dd, 2H), 8.32 (dd, 2H), 10.93 (br.s, 1H)

Example 1

A mixture of 5 ml (46 mmol) of cyclohexane, 0.75 ml of nitrogen dioxide and 0.25 mmol of 4-dodecyloxycarbonyl-N-hydroxyphthalimide was stirred at 70° C. in an atmosphere of air (1 atm=0.1 MPa) for 15 hours and thereby yielded nitrocyclohexane and cyclohexyl nitrate in yields of 40% and 6%, respectively.

Comparative Example 1

The procedure of Example 1 was repeated, except that 0.25 mmol of N-hydroxyphthalimide was used instead of 4-dodecyloxycarbonyl-N-hydroxyphthalimide, and thereby yielded nitrocyclohexane and cyclohexyl nitrate in yields of 26% and 6%, respectively.

Example 2

A mixture of 4 ml (37 mmol) of cyclohexane, 0.1 mmol of 4-dodecyloxycarbonyl-N-hydroxyphthalimide, 0.01 mmol of cobalt(II) acetate and 0.001 mmol of manganese(II) acetate was stirred at 100° C. in an atmosphere of air (30 atm=3 MPa) for 12 hours and thereby yielded 0.05 mmol of cyclohexyl alcohol, 0.15 mmol of cyclohexanone, 2.88 mmol of adipic acid and 0.39 mmol of glutaric acid. The total amount of the four products was 3.47 mmol, and the amount of K/A oil (a mixture of cyclohexyl alcohol and cyclohexanone) was 0.20 mmol.

Comparative Example 2

The procedure of Example 2 was repeated, except that 0.1 mmol of N-hydroxyphthalimide was used instead of 4-dodecyloxycarbonyl-N-hydroxyphthalimide, and thereby yielded 0.06 mmol of cyclohexyl alcohol, 0.1 mmol of cyclohexanone, 0.01 mmol of adipic acid and a trace amount of glutaric acid. The total amount of the four products was 0.17 mmol, and the amount of K/A oil was 0.16 mmol.

Example 3

A mixture of 4 ml (37 mmol) of cyclohexane, 0.1 mmol of 4-dodecyloxycarbonyl-N-hydroxyphthalimide, 0.01 mmol of acetylacetonatocobalt(II) and 0.001 mmol of manganese(II) acetate was stirred at 100° C. in an atmosphere of air (30 atm=3 MPa) for 12 hours and thereby yielded 0.34 mmol of cyclohexyl alcohol, 1.28 mmol of cyclohexanone, 0.27 mmol of adipic acid and 0.13 mmol of glutaric acid. The total amount of the four products was 2.02 mmol, and the amount of K/A oil was 1.62 mmol.

Comparative Example 3

The procedure of Example 3 was repeated, except that 0.1 mmol of N-hydroxyphthalimide was used instead of 4-dodecyloxycarbonyl-N-hydroxyphthalimide, and thereby yielded 0.12 mmol of cyclohexyl alcohol, 0.10 mmol of cyclohexanone, 0.03 mmol of adipic acid and 0.01 mmol of glutaric acid. The total amount of the four products was 0.26 mmol, and the amount of K/A oil was 0.22 mmol.

Example 4

A mixture of 4 ml (37 mmol) of cyclohexane, 0.03 mmol of 4-dodecyloxycarbonyl-N-hydroxyphthalimide, 0.003 mmol of acetylacetonatocobalt(II) and 0.0003 mmol of manganese(II) acetate was stirred at 100° C. in an atmosphere of air (10 atm=1 MPa) for 2 hours and thereby yielded 0.27 mmol of cyclohexyl alcohol, 0.56 mmol of cyclohexanone, 0.05 mmol of adipic acid and 0.02 mmol of glutaric acid. The total amount of the four products was 0.90 mmol, and the amount of K/A oil was 0.83 mmol.

Comparative Example 4

The procedure of Example 4 was repeated, except that 0.03 mmol of N-hydroxyphthalimide was used instead of 4-dodecyloxycarbonyl-N-hydroxyphthalimide, and thereby yielded 0.18 mmol of cyclohexyl alcohol, 0.15 mmol of cyclohexanone, 0.01 mmol of adipic acid and 0.01 mmol of glutaric acid. The total amount of the four products was 0.35 mmol, and the amount of K/A oil was 0.33 mmol.

Example 5

A mixture of 4 ml (37 mmol) of cyclohexane, 0.1 mmol of 4-dodecyloxycarbonyl-N-hydroxyphthalimide, 0.01 mmol of cobalt(II) acetate and 0.001 mmol of manganese(II) acetate was stirred at 100° C. in an atmosphere of air (30 atm=3 MPa) for 2 hours and thereby yielded 0.28 mmol of cyclohexyl alcohol, 1.38 mmol of cyclohexanone, 0.44 mmol of adipic acid and 0.08 mmol of glutaric acid. The total amount of the four products was 2.18 mmol, and the amount of K/A oil (a mixture of cyclohexyl alcohol and cyclohexanone) was 1.66 mmol.

Example 6

A mixture of 4 ml (37 mmol) of cyclohexane, 0.1 mmol of 4-dodecyloxycarbonyl-N-hydroxyphthalimide, 0.01 mmol of acetylacetonatocobalt(II) and 0.001 mmol of manganese(II) acetate was stirred at 100° C. in an atmosphere of air (10 atm=1 MPa) for 2 hours and thereby yielded 0.41 mmol of cyclohexyl alcohol, 1.56 mmol of cyclohexanone, 0.10 mmol of adipic acid and 0.06 mmol of glutaric acid. The total amount of the four products was 2.13 mmol, and the amount of K/A oil was 1.97 mmol.

Example 7

A mixture of 4 ml (37 mmol) of cyclohexane, 0.1 mmol of 4-dodecyloxycarbonyl-N-hydroxyphthalimide, 0.01 mmol of acetylacetonatocobalt(II), 0.001 mmol of manganese(II) acetate and 0.06 mmol of nitrogen dioxide was stirred at 80° C. in an atmosphere of air (10 atm=1 MPa) for 2 hours and thereby yielded 0.30 mmol of cyclohexyl alcohol, 0.65 mmol of cyclohexanone, 0.10 mmol of adipic acid and 0.09 mmol of glutaric acid. The total amount of the four products was 1.14 mmol, and the amount of K/A oil was 0.95 mmol.

Example 8

A mixture of 4 ml (37 mmol) of cyclohexane, 0.03 mmol of 4-dodecyloxycarbonyl-N-hydroxyphthalimide, 0.003 mmol of acetylacetonatocobalt(II) and 0.0003 mmol of manganese(II) acetate was stirred at 100° C. in an atmosphere of air (10 atm=1 MPa) for 2 hours and thereby yielded 0.27 mmol of cyclohexyl alcohol, 0.56 mmol of cyclohexanone, 0.05 mmol of adipic acid and 0.02 mmol of glutaric acid. The total amount of the four products was 0.90 mmol, and the amount of K/A oil was 0.83 mmol.

Example 9

A mixture of 24 mmol of 2-octanol, 0.1 mmol of 4-dodecyloxycarbonyl-N-hydroxyphthalimide and 0.005 mmol of cobalt(II) acetate was stirred at 70° C. in an atmosphere of oxygen gas (1 atm=0.1 MPa) for 3 hours and thereby yielded 1.52 mmol of 2-octanone.

Example 10

A mixture of 47 mmol of toluene, 0.1 mmol of 4-dodecyloxycarbonyl-N-hydroxyphthalimide and 0.01 mmol of acetylacetonatocobalt(II) was stirred at 100° C. in an atmosphere of oxygen gas (1 atm=0.1 MPa) for 6 hours and thereby yielded 1.44 mmol of benzoic acid.

Example 11

A mixture of 4 ml (31 mmol) of n-hexane, 0.03 mmol of 4-dodecyloxycarbonyl-N-hydroxyphthalimide, 0.0003 mmol of acetylacetonatocobalt(II) and 0.003 mmol of manganese(II) acetate was stirred at 100° C. in an atmosphere of air (10 atm=1 MPa) for 2 hours and thereby yielded 0.1 mmol of 2-hexanone, 0.09 mmol of 2-hexanol, 0.04 mmol of 3-hexanone and 0.05 mmol of 3-hexanol.

Comparative Example 5

The procedure of Example 11 was repeated, except that 0.03 mmol of N-hydroxyphthalimide was used instead of 4-dodecyloxycarbonyl-N-hydroxyphthalimide, but no reaction proceeded.

Other embodiments and variations will be obvious to those skilled in the art, and this invention is not to be limited to the specific matters stated above.

What is claimed is:

1. A process for producing an organic compound using a catalyst, the process comprising the step of: allowing a compound (A) capable of forming a radical, said compound (A) being selected from the group consisting of (A1) heteroatom-containing compounds each having a carbon-hydrogen bond at the adjacent position to the heteroatom, (A2) compounds each having a carbon-heteroatom double bond, (A3) compounds each having a methine carbon atom, (A4) compounds each having a carbon-hydrogen bond at the adjacent position to an unsaturated bond, (A5) non-aromatic cyclic hydrocarbons, (A6) conjugated compounds, (A7) amines, (A8) aromatic compounds, (A9) straight-chain alkanes and (A10) olefins, to react with a radical scavenging compound (B), said compound (B) being selected from the group consisting of (B1) unsaturated compounds, (B2) compounds each having a methine carbon atom, (B3) heteroatom-containing compounds and (B4) oxygen-atom-containing reacting agents, in the presence of a catalyst, the catalyst comprising a cyclic imide compound, the cyclic imide compound having an N-substituted cyclic imide skeleton represented by following Formula (II):

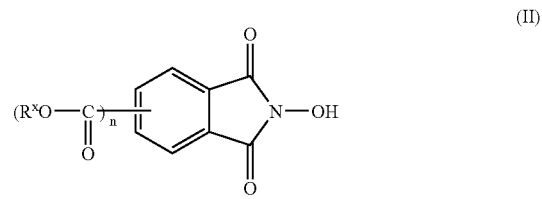

wherein $R^x$ is a hydrocarbon group having five or more carbon atoms; and n denotes an integer of from 1 to 4, where the groups —C(=O)—OR$^x$ may be the same or different when n is equal to or more than 2, said cyclic imide compound having a solubility parameter of less than or equal to 26 (MPa)$^{1/2}$ as determined by Fedors method to thereby yield a product of an addition or substitution reaction between the compound (A) and the compound (B) or a product of a dehydration reaction, a cyclization reaction, a decarboxylation reaction, a rearrangement reaction or an isomerization reaction thereof.

2. The process according to claim 1, wherein the oxygen-atom-containing reacting agents (B4) are at least one selected from the group consisting of oxygen, carbon monoxide, nitrogen oxides, sulfur oxides, and nitric acid, nitrous acid or salts thereof.

3. The process according to claim 1, wherein the reaction between the compound (A) capable of forming a radical and the radical scavenging compound (B) is one selected from the group consisting of oxidation reactions, carboxylation reactions, nitration reactions, sulfonation reactions, coupling reactions and combinations thereof.

4. The process according to claim 1, wherein the catalyst further comprises a metal compound.

* * * * *